US012790605B2

(12) United States Patent
Forbes et al.

(10) Patent No.: US 12,790,605 B2
(45) Date of Patent: Nov. 10, 2026

(54) METHOD OF TRANSFECTING MACROPHAGES

(71) Applicant: The University Court of The University of Edinburgh, Edinburgh (GB)

(72) Inventors: Stuart Forbes, Edinburgh (GB); Lara Campana, Edinburgh (GB); Benjamin Dwyer, Edinburgh (GB); Philip Starkey Lewis, Edinburgh (GB); John Campbell, Edinburgh (GB); Alasdair Fraser, Edinburgh (GB)

(73) Assignee: The University Court of The University of Edinburgh, Edinburgh (GB)

( * ) Notice: Subject to any disclaimer, the term of this patent is extended or adjusted under 35 U.S.C. 154(b) by 591 days.

(21) Appl. No.: 17/927,793

(22) PCT Filed: May 27, 2021

(86) PCT No.: PCT/GB2021/051300

§ 371 (c)(1),
(2) Date: Nov. 25, 2022

(87) PCT Pub. No.: WO2021/240167

PCT Pub. Date: Dec. 2, 2021

(65) Prior Publication Data

US 2023/0265389 A1 Aug. 24, 2023

(30) Foreign Application Priority Data

May 27, 2020 (GB) ...................................... 2007906

(51) Int. Cl.

| | |
|---|---|
| ***C12N 13/00*** | (2006.01) |
| ***A61K 40/17*** | (2025.01) |
| ***A61K 40/24*** | (2025.01) |
| ***A61K 40/40*** | (2025.01) |
| ***C12N 5/0786*** | (2010.01) |
| ***C12N 15/85*** | (2006.01) |

(52) U.S. Cl.

CPC .............. *C12N 13/00* (2013.01); *A61K 40/17* (2025.01); *A61K 40/24* (2025.01); *A61K 40/40* (2025.01); *C12N 5/0645* (2013.01); *C12N 15/85* (2013.01); *A61K 2239/31* (2023.05); *A61K 2239/38* (2023.05); *C12N 2800/107* (2013.01)

(58) Field of Classification Search

None

See application file for complete search history.

(56) References Cited

U.S. PATENT DOCUMENTS

2018/0100161 A1* 4/2018 Sixto ........................ C12N 5/10

FOREIGN PATENT DOCUMENTS

WO 2019118888 A1 6/2019

OTHER PUBLICATIONS

Somiari et al. Theory and in Vivo Application of Electroporative Gene Delivery. Mol Ther. Sep. 2000;2(3):178-87. (Year: 2000).*

Luft et al. Electroporation Knows No Boundaries: The Use of Electrostimulation for siRNA Delivery in Cells and Tissues. J Biomol Screen. Sep. 2015;20(8):932-942. (Year: 2015).*

Zhang et al. The Expression of Exogenous Genes in Macrophages: Obstacles and Opportunities. Methods Mol Biol. 2009:531:123-43. (Year: 2009).*

Demiryurek et al. Transport, resealing, and re-poration dynamics of two-pulse electroporation-mediated molecular delivery. Biochim Biophys Acta. Aug. 2015;1848(8):1706-14. Epub Apr. 22, 2015. (Year: 2015).*

PCT International Search Report, mailed Aug. 27, 2021, in connection with International Application No. PCT/GB2021/051300, all pages.

PCT Written Opinion, mailed Aug. 27, 2021, in connection with International Application No. PCT/GB2021/051300, all pages.

Maess, M.B. et al., "Optimization of the transfection of human THP-1 macrophages by application of Nunc UpCell technology", ScienceDirect, Analytical Biochemistry, vol. 479, Jun. 15, 2015, pp. 40-42.

Porcheray, F. et al., "Macrophage activation switching: an asset for the resolution of inflammation", Clinical and Experimental Immunology, 142, Oct. 6, 2005, pp. 481-489.

Martinet, W. et al., "Nucleofection as an efficient nonviral transfection method for human monocytic cells", Biotechnology Letters, 25, Jul. 1, 2003, pp. 1025-1029.

Fraser, A.R. et al., "Development, functional characterization and validation of methodology for GMP-compliant manufacture of phagocytic macrophages: A novel cellular therapeutic for liver cirrhosis", Cytotherapy, vol. 19, No. 9, Sep. 1, 2017, pp. 1113-1124.

Great Britain Search Report issued Mar. 22, 2021 in connection with Great Britain Application No. GB2007906.7, 2 pages.

* cited by examiner

*Primary Examiner* — Valarie E Bertoglio
*Assistant Examiner* — Briana N Ebbinghaus
(74) *Attorney, Agent, or Firm* — Morrison & Foerster LLP

(57) ABSTRACT

The development of the method of the invention enables the efficient and reproducible production of genetically modified GMP-grade human macrophages. The inventors have described the effects of the method described on cell viability and efficiency of introduction of genetic material into macrophages. Unlike previous methods of introducing genetic material into macrophages, excellent conditions are demonstrated which produce efficient transgene expression, without compromising cell viability. Critically, the method of the invention does not use virus to introduce genetic material, is efficacious on mature cells, are functional with in vitro assay and in vivo transfer in a liver disease model and complies with practices compatible with manufacture and delivery of these cells to patients.

7 Claims, 9 Drawing Sheets

Figure 1A:
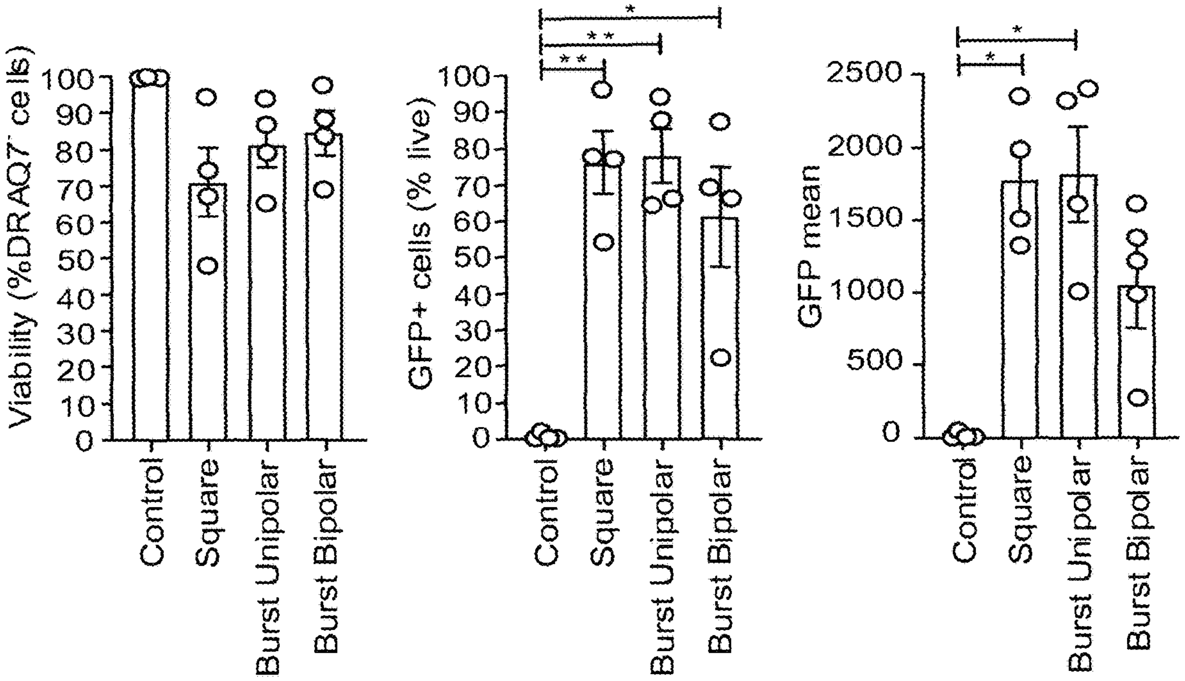

First pulse modes (950V) without second low-voltage burst pulse

METHOD OF TRANSFECTING MACROPHAGES

CROSS-REFERENCE TO RELATED APPLICATIONS

This application is a national stage entry of PCT International Application No. PCT/GB2021/051300, filed May 27, 2021, which claims benefit of priority to GB Application No. 2007906.7, filed May 27, 2020, which are incorporated herein by reference in their entireties.

FIELD OF THE INVENTION

The present invention relates to a method of transfecting human macrophages with genetic material which is based on a two-step method of electroporation. The present invention further relates to transfected macrophages, macrophages transfected by the method, populations thereof, and medical uses of the transfected macrophages.

INTRODUCTION TO THE INVENTION

Genetic modification of cell therapy products is desirable in order to confer specific therapeutic functions to the therapeutic cells by modulation of their gene expression. Modification of the gene expression of the therapeutic cells positively affects the function of the cell therapy product and can modulate the environment into which the cells are introduced as a therapy. This approach has proven successful for producing novel, engineered cell therapy products such as genetically modified autologous T-cells for cancer therapy [1].

Transfection is defined as the transfer of heterologous nucleic acid into cells. However, macrophages are considered as hard-to-transfect cells, as they have, by their very nature, evolved to recognise foreign nucleic acid and initiate an immune response to such molecules. Therefore, it is hard to transfect macrophages whilst avoiding their activation. Advances in technology allows different types of nucleic acids to be transfected into mammalian cells, and these include Deoxyribonucleic acids (DNAs), Ribonucleic acids (RNAs) as well as small, non-coding RNAs such as small interfering RNAs (siRNAs), short hairpin RNAs (shRNAs), and microRNAs (miRNAs).

Macrophages have proven efficacious as a potential cell therapy in a number of pre-clinical models of various human diseases. We have demonstrated efficacy of ex vivo-differentiated macrophages in reduce scarring in rodent models of liver cirrhosis [2,3], and have further shown delivery of autologous monocyte-derived macrophages to patients with liver cirrhosis is safe [4]. However, genetically modified human macrophages have historically been difficult to produce with appropriate efficiency and viability, especially using methods that are compatible with human therapeutic administration.

To overcome the difficulty in modifying macrophages, alternative approaches have been investigated. One suggested approach is to genetically modify the precursor cells, such as monocytes or pluripotent cells. Monocytes have been genetically modified using transduction with replication-incompetent viruses to deliver exogenous constructs and the cells subsequently differentiated into macrophages (US patent US20170087185A1, [5]). However, this method has the theoretical potential for recombination events to occur resulting in replication-competent virus [6] and insertional mutagenesis events that raise the risk of neoplastic transformation and cell therapy-derived cancers [7]. Another approach which is currently being investigated is the modification of pluripotent cells, such as iPS or ES cells, which are capable of being differentiated into macrophage-like cells containing the genetic modification [8,9]. However, the use of pluripotent cells also brings with it the risks of tumorigenesis associated with using a pluripotent cell source [10]. A non-viral method to produce genetically modified macrophages from non-pluripotent sources would overcome these safety concerns, but has not yet been achieved.

An attractive alternative to viral methods of genetic modification is to use non-integrating methods to introduce episomal constructs, such as plasmid DNA, to express genes of interest within the macrophages. Several non-viral methods are available to introduce genetic material including forms of lipofection or electroporation. As electroporation is compatible with Good Manufacturing Practice (GMP) manufacturing protocols, it could be a potential route to producing clinically useful cell products. However, current methods of macrophage electroporation result in unsuitable levels of cell death [11, 12], low efficiency [11-14], or are only amenable to transfecting non-human macrophage sources [11, 13, 15] and cell lines [14], precluding their use for producing genetically modified primary macrophages for cell therapy in humans. In particular, success with primary human cells that could be used for cell therapy has not been achieved, and the lack of methods to produce therapeutic-grade genetically modified human macrophages remains a hurdle to clinical translation.

The development of the method of the invention enables the efficient and reproducible production of genetically modified GMP-grade macrophages, notably primary human monocyte-derived macrophages. The inventors have described the effects of the method described on cell viability and efficiency of introduction of genetic material into macrophages. Unlike previous methods of introducing genetic material into macrophages, they demonstrate excellent conditions which produce efficient transgene expression, without compromising cell viability. Critically, the method of the invention do not use viruses to introduce genetic material, is efficacious on mature cells, are functional with in vitro assay and in vivo transfer in a liver disease model and complies with practices compatible with manufacture and delivery of these cells to patients.

One or more aspects or embodiments of the claimed invention aim to solve one or more of the above-mentioned problems.

STATEMENTS OF INVENTION

According to a first aspect of the present invention, there is provided a method of transfecting a human macrophage with genetic material, the method comprising the steps of:

(a) Contacting a human macrophage with genetic material;

(b) Electroporating the macrophage with a first pulse phase, wherein the first pulse phase comprises a burst of unipolar pulses or a square pulse, wherein each pulse is between 750-1000V, and wherein the first pulse phase lasts for a total period of between 20-500 μs; and (c) Electroporating the macrophage with a second pulse phase, wherein the second pulse phase comprises a burst of pulses or a square pulse, wherein each pulse is between 50-225V, and wherein the second pulse phase lasts for a total period of 2000-50000 μs.

According to a second aspect of the present invention, there is provided a transfected human macrophage produced by the method of the first aspect.

According to any aspect of the invention, the genetic material may be a nucleic acid, optionally a heterologous nucleic acid. According to a third aspect of the present invention, there is provided a transfected human macrophage comprising a heterologous nucleic acid, wherein the macrophage has a repressed Stimulator of Interferon Genes (STING) pathway. In one embodiment, the repression of the STING pathway is caused by directly inhibiting one or more components of the STING pathway, suitably therefore the transfected human macrophage has a repressed STING pathway.

In one embodiment, the repression of the STING pathway occurs after transfection according to the methods of the invention. In an alternative embodiment, the repression of the STING pathway occurs before or during transfection.

In one embodiment, the repression of the STING pathway is caused by the macrophage being polarized, suitably therefore the transfected human macrophage is polarized. In one embodiment, the transfected macrophage has reduced expression of IFN-β.

In one embodiment, the repression of the STING pathway is caused by the macrophage being contacted with IL4+IL13, or IL10. Optionally, the macrophage is contacted with IL4+IL13, or IL10 after the transfection method of the invention.

In one embodiment, the heterologous nucleic acid is non-viral.

According to a fourth aspect of the present invention there is provided a population of transfected human macrophages according to the second or third aspects of the invention.

According to a fifth aspect of the present invention, there is provided a population of transfected human macrophages, wherein the viability of the population is at least 60%.

In one embodiment, the macrophages of the population comprise a heterologous nucleic acid. In one embodiment, the heterologous nucleic acid is non-viral.

In one embodiment, the macrophages of the population have reduced expression of IFN-β.

In one embodiment, the macrophages of the population have a repressed STING pathway.

In one embodiment, the macrophages of the population are polarized.

According to a sixth aspect of the present invention, there is provided a transfected human macrophage produced by the method of the first aspect for use as a medicament.

According to an alternative sixth aspect of the present invention, there is provided a method of treating a subject in need thereof, comprising administering an effective amount of the transfected human macrophage of the first aspect to the subject.

According to a seventh aspect of the present invention, there is provided a transfected human macrophage according to the third aspect of the present invention, or a population of transfected human macrophages according to the fourth or fifth aspects for use as a medicament. Alternatively defined, said macrophages are for use in therapy.

In one embodiment, the transfected human macrophage or the population of transfected human macrophages are for use in the treatment of a liver disease.

According to an alternative seventh aspect of the present invention there is provided a method of treating a subject in need thereof, comprising administering an effective amount of a transfected human macrophage according to the third aspect of the present invention, or a population of transfected human macrophages according to the fourth or fifth aspects to a subject.

In one embodiment, the method is for treating a subject having a liver disease.

In an eighth aspect of the present invention there is provided use of transfected human macrophages according to the second or third aspects, or a population of transfected human macrophages according to the fourth or fifth aspects, in the manufacture of a medicament for treating a disease in a subject, the manufacture comprising:

(a) Contacting a human macrophage with genetic material;

(b) Electroporating the macrophage with a first pulse phase, wherein the first pulse phase comprises a burst of unipolar pulses or a square pulse, wherein each pulse is between 750-1000V, and wherein the first pulse phase lasts for a total period of between 20-500 μs; and (c) Electroporating the macrophage with a second pulse phase, wherein the second pulse phase comprises a burst of pulses or a square pulse, wherein each pulse is between 50-225V, and wherein the second pulse phase lasts for a total period of 2000-50000 μs; and (d) Formulating some or all of said macrophages into a medicament for administration to the subject.

In one embodiment, the disease is a liver disease.

The present inventors have developed a novel method of directly transfecting human macrophages which is non-viral and compatible with GMP, and which manages to maintain high levels of cell viability within the population of transfected macrophages. The method is based on two steps of electroporation at different optimal settings which were discovered by the inventors. In order to derive the inventive electroporation protocol, the inventors generated human monocyte-derived macrophages using GMP-compliant reagents and conditions and undertook a comprehensive assessment of various unique pulse combinations to electroporate an exemplary plasmid encoding GFP into the macrophages. Electroporation efficacy and cell viability were analysed by flow cytometry. The inventors optimised the electroporation protocol to generate genetically modified human macrophages that show high population viability and high population transfection rates by expression of fluorescent GFP protein as a proof of concept of GMP-compatible production of genetically modified human macrophages. The results demonstrated herein show that the optimised protocol of the invention can be used to modify human macrophages to express genes of interest and to provide an effective cell-therapy product. In addition, the method avoids the safety issues with previously-used viral transfection methods, and directly transfects human macrophages without needing to add further differentiation protocols as with prior methods based on transfecting precursor cells.

The invention will now be described further with reference to the following headed sections. Any features under any of the sections may be combined with any of the aspects or embodiments of the invention in any workable order.

DESCRIPTION

The following definitions are provided.

'hMDM' as used in the present invention refers to human monocyte derived macrophages. Monocyte-derived means macrophages differentiated from monocytes. Monocytes are the natural precursors of macrophages and dendritic cells, they are contained in blood and bone marrow.

'unpolarized macrophage' as used in the present invention refers to a mature macrophage which has not received any further stimulation to induce particular functional capacity, unpolarized macrophages may also refer to naïve or non-activated macrophages.

'polarized macrophage' as used in the present invention refers to a macrophage which has received environmental stimulus to become activated into a particular phenotype such as the M1-like or M2-like phenotype. The M1-like and M2-like phenotypes are described hereinbelow.

'macrophage' refers to a phagocytic cell which is responsible for detecting, engulfing and destroying pathogens and apoptotic cells, and which is produced through the differentiation of monocytes. The term refers to a macrophage which may be polarized or unpolarized.

'mature macrophage' refers to a macrophage which expresses mature cell surface markers, preferably CCR2−, CD14+, CD206+, CD163+, CD169+, 25F9+, and CD86+.

An 'M1 polarising factor' as used in the present invention refers to a factor which stimulates an unpolarized macrophage into an M1-like phenotype, and may refer to one or more of: GM-CSF, INFγ, and TLR agonists, such as LPS, for example.

An 'M2 polarising factor' as used in the present invention refers to a factor which stimulates an unpolarized macrophage into an M2-like phenotype, and may refer to one or more of: IL10, IL4, IL13, and poly(I:C), for example.

'GMP-compliant' as used in the present invention means that the method complies with Good Manufacturing Practice principles and may be used interchangeably with 'GMP-compatible'. By way of example a GMP-compliant medium has to be serum-free, antibiotic-free, animal substance free and xenoprotein-free. The WHO provides guidance on what is required for good manufacturing practice: "Chapter 1: WHO good manufacturing practices: Main principles for pharmaceutical products". *Quality Assurance of Pharmaceuticals: A compendium of guidelines and related materials—Good manufacturing practices and inspection.* 2 (2nd updated ed.). WHO Press. pp. 17-18. ISBN 9789241547086.

'treatment' as used in the present invention means an intervention in a physiological condition which prevents, reduces or removes the clinical symptoms associated with a given physiological condition in a subject.

By 'subject' or 'individual' or 'animal' or 'patient' is meant any subject, particularly a mammalian subject, for whom diagnosis, prognosis, or therapy is desired, except where the subject is defined as a 'healthy subject'. Mammalian subjects include humans; domestic animals; farm animals; such as dogs, cats, guinea pigs, rabbits, rats, mice, horses, cattle, cows, and so on.

'day5 no feed' or 'day5' as used in the present invention in relation to a method/protocol refers to a method/protocol to produce macrophages, which lasts between 3 to 5 days, optionally 4-5 days. 3-5 days typically refers to a period of about 72-120 hours. 4-5 days typically refers to a period of about 96-120 hours. These periods may vary by +/−10 hours, preferably +/−5 hours, preferably +/−2 hours. Suitably therefore, the method of the invention may last between 62 and 130 hours, suitably between 86 and 130 hours, suitably between 90 and 125 hours, suitably between 96 and 120 hours. 'day7 plus re-feed' or 'day7' as used in the present invention in relation to a method/protocol refers to a longer method/protocol to produce macrophages. These methods last for a period of around 7 days which typically refers to a period of about 168 hours. This period may vary by +/−10 hours, preferably +/−5 hours, preferably +/−2 hours.

It is to be noted that the term "a" or "an" entity refers to one or more of that entity.

'about' means+/−10% of the value given, +/−9%, +/−8%, +/−7%, +/−6%, +/−5%, +/−4%, +/−3%, +/−2%, +/−1%, unless otherwise stated.

Human Macrophages

The invention relates to a method of transfecting human macrophages with genetic material so as to produce transfected human macrophages that are genetically modified and can be used for cell therapy.

Suitably the macrophages are isolated from a subject.

Suitably the macrophages are monocyte derived. Suitably they are human monocyte derived macrophages (hMDM). Suitably the macrophages are derived from peripheral blood monocytes, suitably the macrophages are peripheral blood monocyte derived macrophages. Suitably the macrophages are human peripheral blood monocyte derived macrophages.

Suitably, in one embodiment, the method may comprise a further preliminary step of deriving human macrophages from human monocytes.

Suitably the macrophages are derived from the monocytes by culturing the monocytes, suitably in vitro. Suitably the macrophages are derived from the monocytes by using any suitable culturing method.

Suitably the macrophages have been produced in vitro.

Suitably the macrophages have been produced in vitro from any suitable progenitor cell. Suitably, the macrophages have been produced from stem cells, such as induced pluripotent stem cells.

Suitably the method of the invention may further comprise a step of obtaining macrophages. Suitably such a step takes place before step (a) of the method of transfecting macrophages. Suitably, the macrophages may be obtained from any suitable source.

Suitably this step may comprise producing macrophages in vitro. Suitably this step may comprise producing macrophages from monocytes in vitro.

Suitably, in one embodiment, the method may comprise a further preliminary step of culturing human monocytes to produce human macrophages.

In one embodiment, the method may comprise the steps of:

(a) Culturing a human monocyte to produce a human macrophage;
(b) Contacting a human macrophage with genetic material;
(c) Electroporating the macrophage with a first pulse phase, wherein the first pulse phase comprises a burst of unipolar pulses or a square pulse, wherein each pulse is between 750-1000V, and wherein the first pulse phase lasts for a total period of between 20-500 μs; and
(d) Electroporating the macrophage with a second pulse phase, wherein the second pulse phase comprises a burst of pulses or a square pulse, wherein each pulse is between 50-225V, and wherein the second pulse phase lasts for a total period of 2000-50000 μs.

Suitably, therefore, the method of the invention may further comprise a step of obtaining monocytes.

Suitably the human monocytes are provided from any source such whole blood, mononuclear cells, leukapheresis or they may be iPSC-derived. Suitably the sample of human whole blood or other source may be fractionated to provide mononuclear cell fraction. Suitably the monocytes are obtained from the mononuclear leukocyte fraction of human blood, suitably from the mononuclear leukocyte fraction of a human blood sample.

Suitably the methods may further comprise a step of purifying monocytes from blood, suitably from the mononuclear leukocyte fraction of blood, suitably from the mononuclear leukocyte fraction of a human blood sample. Such purification may comprise isolation of the mononuclear leukocyte fraction, and isolation of purified monocytes from the fraction using specific (markers of monocyte lineage) or non-specific (adherence) methods. Suitably isolation of the mononuclear leukocyte fraction may be carried out by various methods depending upon source material. Suitably isolation of selected purified monocytes may be carried out at small scale (magnetic bead column devices or plastic adherence) or at larger scale for manufacturing using relevant devices such as the CliniMACS Prodigy system (Miltenyi Biotec).

Suitably the monocytes are isolated from whole blood or other cell source as above, suitably by enrichment. Suitably isolation of mononuclear cell fractions may be carried out by density centrifugation or microfluidic separation of the source material. Suitably isolation of purified monocytes may be carried out by filtration of the mononuclear cell fraction, such as for example magnetic bead to a surface marker specific for monocytes with column filtration, suitable filtration systems include the CliniMACS Prodigy system (Miltenyi Biotec). Suitably isolation of purified monocytes may be carried out by CD14 microbead selection.

Suitably therefore, the method of the invention may comprise a step of obtaining monocytes from a sample of blood. Suitably therefore, the method of the invention may comprise a step of obtaining monocytes from a sample of human blood. Suitably therefore, the method of the invention may comprise a step of isolating monocytes from a sample of blood. Suitably therefore, the method of the invention may comprise a step of isolating monocytes from a sample of human blood.

Suitably the monocytes are positive for the expression of the following surface markers-CD14, CD45 and CD192 (CCR2). Suitably the isolated monocytes have low expression of surface marker 25F9 (or the identified molecule recognised by this antibody) and CD206. Suitably the monocytes have high expression of CCR2.

Suitably, in one embodiment, the method may comprise a further preliminary step of providing human monocytes. Suitably, the method may comprise a further preliminary step of isolating human monocytes from whole blood or other suitable cell source.

In one embodiment, the method may comprise the steps of:

(a) Providing a human monocyte;
(b) Culturing the human monocyte to produce a human macrophage;
(c) Contacting a human macrophage with genetic material;
(d) Electroporating the macrophage with a first pulse phase, wherein the first pulse phase comprises a burst of unipolar pulses or a square pulse, wherein each pulse is between 750-1000V, and wherein the first pulse phase lasts for a total period of between 20-500 μs; and
(e) Electroporating the macrophage with a second pulse phase, wherein the second pulse phase comprises a burst of pulses or a square pulse, wherein each pulse is between 50-225V, and wherein the second pulse phase lasts for a total period of 2000-50000 μs.

Suitably the monocyte may be cultured to form a macrophage and may be electroporated to form a transfected macrophage within one method. Suitably therefore, the method from monocyte to transfected macrophage may take place in one system, suitably in an enclosed system. Suitably the entire method from monocyte to transfected macrophage may take place in the CliniMACS Prodigy system (Miltenyi Biotec). Advantageously, the inventors have further been able to carry out differentiation of monocytes into macrophages and then transfection of macrophages within a single system, whereas prior art methods involve several separate systems.

In a further aspect of the invention, there is provided a method of transfecting a human macrophage comprising the steps of:

(a) Providing a human monocyte;
(b) Culturing the human monocyte to produce a human macrophage;
(c) Contacting a human macrophage with genetic material; and
(d) Electroporating the human macrophage;

wherein the method takes place in an enclosed system.

In one embodiment, step (d) of electroporating the human macrophages comprises the steps of the first aspect of the invention.

In one embodiment, the method may comprise the steps of:

(a) Providing a human monocyte;
(b) Culturing the human monocyte to produce a human macrophage;
(c) Contacting a human macrophage with genetic material;
(d) Electroporating the macrophage with a first pulse phase, wherein the first pulse phase comprises a burst of unipolar pulses or a square pulse, wherein each pulse is between 750-1000V, and wherein the first pulse phase lasts for a total period of between 20-500 μs; and
(e) Electroporating the macrophage with a second pulse phase, wherein the second pulse phase comprises a burst of pulses or a square pulse, wherein each pulse is between 50-225V, and wherein the second pulse phase lasts for a total period of 2000-50000 μs;

wherein the method takes place in an enclosed system.

As used herein, an enclosed or closed system may be used. Such means that the method may be carried out in a closed system from start to finish, usually under GMP conditions. A closed (or enclosed) system is a process system with equipment designed and operated such that the cells are not exposed to the room environment. Such does not preclude additions to the closed system, these just need to be made in such a way that the cells are not exposed to the room environment, for example by use of filters of the appropriate size.

Suitably the human macrophages may be transfected for the purpose of making a macrophage-based cell therapy. Suitably in such embodiments, the human macrophages may be autologous or allogeneic to the subject to eventually be treated with the macrophages. Suitably, in such embodiments, the human macrophages may be obtained from a blood sample from a subject to eventually be treated with the transfected macrophages, or from a suitable donor source for allogeneic treatment. Suitably therefore the methods of the invention are methods of transfecting macrophages for autologous or allogeneic use, and the transfected macrophages for use in the medical methods of the invention are transfected macrophages for autologous or allogeneic use.

Suitably any method of culturing may be used to convert the monocytes into macrophages. Suitable such culturing methods are discussed below.

Suitably the macrophages are derived from monocytes by culturing monocytes in medium supplemented with one or more growth factors. Suitably by culturing monocytes in medium selected from: XVivo 10, TexMACS, AIMv, RPMI, DMEM, and DMEM/F12. Suitably the medium is TexMACS (Miltenyi).

Suitably the medium is serum-free. Suitably the medium is xenoprotein-free. Suitably the medium is GMP-compliant.

Suitably the medium may contain one or more factors. Suitable factors include growth factors, polysaccharides, cytokines and chemokines. Suitable factors may include: M-CSF, GM-CSF.

Suitably the medium contains a growth factor, suitably M-CSF (macrophage colony stimulating factor) otherwise known as CSF-1. Suitably the M-CSF may be recombinant M-CSF, suitably recombinant human M-CSF.

Suitably the medium is supplemented with M-CSF. Suitably the M-CSF may be at a concentration of 25-150 ng/ml, suitably at a concentration of between 50-125 ng/ml, suitably at a concentration of between 75-110 ng/ml suitably at a concentration of 100 ng/ml. Suitably, 100 ng of recombinant human M-CSF GMP-graded=$1.6\times10^4$ IU.

Suitably the monocytes may be cultured until mature macrophages are formed.

Suitably the macrophages are produced in vitro from monocytes by a culturing method lasting between 3 to 8 days optionally 4 to 8 days. Suitably the macrophages are produced in vitro from monocytes by a culturing method lasting between 3 to 7 days, notably 4 to 7 days, or 5 to 7 days. In one embodiment, the macrophages are produced in vitro from monocytes by a culturing method that lasts 3-5 days, 4 or 5 days, or 7 days, known as a day5 method or a day7 method, respectively. One example of an in vitro method of producing macrophages from monocytes is described in WO2019/175595. The 'day5' method is described in co-pending application No PCT/GB2021/051294.

In one embodiment, the macrophages are produced by a 'day5' method comprising:

(a) Culturing monocytes in medium for 3-5 or 4-5 days to produce macrophages, wherein the medium comprises one or more growth factors to stimulate macrophage production;

wherein step (a) takes place entirely in the same medium.

Suitably the medium comprises one or more growth factors selected from the CSF family, preferably M-CSF.

Suitably the medium contains M-CSF at a concentration of between 25-150 ng/ml.

Suitably the macrophages may be produced from any progenitor cells such as monocytes (as described above) alternatively from stem cells, inducible pluripotent stem cells and the like.

Suitably, the macrophages are produced from human progenitor cells. Suitably from monocytes, suitably human monocytes. Suitably therefore, producing macrophages in vitro comprises culturing progenitor cells. Suitably therefore producing macrophages in vitro comprises culturing human progenitor cells. Suitably therefore producing macrophages in vitro comprises culturing human monocytes.

In one embodiment, producing macrophages in vitro comprises culturing human monocytes for 3, 4, or 5 days.

Suitably therefore, the method of the invention may comprise a step of culturing monocytes in vitro to produce macrophages. Suitably therefore, the method of the invention may comprise a step of culturing human monocytes in vitro to produce macrophages. Suitably therefore, the method of the invention may comprise a step of culturing human monocytes in vitro to produce macrophages for a period of between 3-8 days, optionally 4-8 days, suitably 3, 4, or 5 days.

Suitably the monocytes may be cultured in medium within tissue culture plates or within expansion bags.

Suitably the monocytes are seeded at a density of $1\times10^6$ cells/cm$^2$ up to $1\times10^8$ cells/cm$^2$, suitably at a density of $5\times10^6$ cells/cm$^2$ up to $5\times10^7$ cells/cm$^2$, suitably at a density of $7\times10^6$ cells/cm$^2$.

Suitably, the cell culture bag is GMP-graded.

Suitably, the monocytes are cultured in the cell culture bag at densities of at least $1\times10^6$/cm$^2$, at least $2\times10^6$/cm$^2$ or at least $3\times10^6$/cm$^2$.

Suitably the monocytes are cultured in a humidified atmosphere.

Suitably the monocytes are cultured at a temperature of 35° C. to 39° C., suitably of 36° C. to 38° C., suitably at about 37° C.

Suitably the monocytes are cultured in an atmosphere comprising air with additional carbon dioxide.

Suitably the carbon dioxide is at a concentration of 1-20%, suitably 2-15%, suitably 3-10%, suitably 4-8%, suitably about 5%.

Suitably the human macrophages express typical mature macrophage cell markers. Suitably the macrophages are characterised by one or more of the following cell markers; CD14+, CD206+, CD163+, CD169+, 25F9+, and CD86+. Suitably the macrophages are CCR2−.

Suitably the macrophages have phagocytic capacity. Suitably the macrophages have the expected phagocytic capacity for mature macrophages. Suitably the macrophages have a cytoplasmic MFI of between 20-65 after 140 minutes of phagocytosis, of between 30-55 after 140 minutes of phagocytosis, of between 35-50 after 140 minutes of phagocytosis, of about 40 after 140 minutes of phagocytosis. Suitably the cytoplasmic MFI is measured by incubating the macrophages with pH sensitive fluorescent beads for 1 hour and measuring the emitted fluorescence as explained in the examples.

Suitably the macrophages respond to inflammatory stimuli. Suitably the macrophages have the expected response to inflammatory stimuli. Suitably the macrophages respond to inflammatory stimuli such as: IFNγ, IL10, IL4, IL13, and LPS.

Suitably the macrophages have low adhesion to surfaces. Suitably the macrophages have a lower adhesion to surfaces than macrophages produced by prior art methods. Suitably the percentage of adherent macrophages is lower than 80%, lower than 75%, lower than 70%, lower than 65%, lower than 60%, lower than 55%, lower than 50%, lower than 45%. Suitably the percentage of adherent cells is calculated by (number of plated cells pre-incubation and washing/number of harvested cells post-incubation and washing) *100. Suitably, these values are calculated as the number of macrophages that are able to adhere to a plastic surface in the span of 2 hours, at 37° C. and 5% CO2. For example, a 70% adhesion means that 70% of the macrophages seeded onto the plate are attached to it after 2 hours.

Suitably the macrophages retain the characteristic cell surface markers, the phagocytic capacity, the response to inflammatory stimuli and the low adhesion after the method of the invention is performed.

Suitably therefore the transfected macrophages produced by the invention retain all of the above properties.

Suitably, in most embodiments, the human macrophages are unpolarized. Suitably, the macrophages are mature. Alternatively, the macrophages may be polarized. Suitably the human macrophages may be polarized, suitably into M1-like or M2-like macrophages. Suitably the macrophages may be polarized before or after the method of transfection. Suitably therefore, the method may comprise transfecting human polarized macrophages, suitably transfecting human M1-like or M2-like macrophages. Alternatively, the method may comprise a step of polarization of the transfected macrophages, suitably polarization of the transfected human macrophages into M1-like or M2-like transfected human macrophages.

Suitably the M1-like and the M2-like phenotype are generated by polarization with various factors.

Suitably the M1-like phenotype is pro-inflammatory.

Suitably the M2-like phenotype is pro-restorative.

Suitably the medium may be supplemented with polarization factors. Suitably such factors stimulate the macrophages to develop into polarized macrophages. Suitably the medium may be supplemented with factors for M1-like polarization or factors for M2-like polarization.

Suitably in order to produce M1-like macrophages the one or more polarising factors may include: GM-CSF, IFNγ, and TLR agonists such as LPS. In one embodiment the M1 polarising factor is IFNγ.

Suitably in order to produce M2-like macrophages the one or more polarising factors may include: IL-10, IL-4, IL-13 and poly(I: C). In one embodiment the M2 polarising factors are IL-4 and IL-13.

Alternatively, the M2 polarising factor is IL10.

Suitably the concentration of each polarising growth factor added to the medium is between 10-150 ng/mL, suitably between 25-125 ng/ml, suitably between 50-100 ng/ml.

Suitably the medium may contain M1 polarization factors at a concentration of between 10-100 ng/ml, suitably at a concentration of between 20-80 mg/ml, suitably at a concentration of between 30 ng/ml to 60 ng/ml, suitably at a concentration of 50 ng/ml. In one embodiment the M1 polarising growth factor is IFNγ used at a concentration of 50 ng/ml (equivalent to $0.1\times10^4$ IU/mL).

Suitably the medium may contain M2 polarization factors at a concentration of between 1-20 ng/ml, suitably at a concentration of between 5-15 mg/mL, suitably at a concentration of between 8 ng/ml to 12 ng/ml, suitably at a concentration of 10 ng/ml. In one embodiment the M2 polarising factors are IL4 and IL13 μsed at a concentration of 10 ng, or $0.29\times10^3$ IU.

Suitably the concentration of each M1 polarising factor is about 50 ng/ml.

Suitably the concentration of each M2 polarising factor is about 10 ng/ml.

Suitably during the polarization step, further M-CSF is added to the media.

Suitably the further M-CSF is added to the medium at a concentration of between 10-150 ng/ml, suitably at between 25-125 ng/ml, suitably between 50-100 ng/ml. Suitably further M-CSF is added to the medium at a concentration of about 50 ng/ml. Suitably 100 ng of recombinant human M-CSF GMP-graded=$1.6\times10^4$ IU.

Suitably, in one embodiment, the method may comprise a further preliminary step of polarising human macrophages, suitably into human M1-like or M2-like macrophages.

In one embodiment, the method may comprise the steps of:

(a) Polarising a human macrophage;

(b) Contacting the human polarized macrophage with genetic material;

(c) Electroporating the macrophage with a first pulse phase, wherein the first pulse phase comprises a burst of unipolar pulses or square pulse, wherein each pulse is between 750-1000V, and wherein the first pulse phase lasts for a total period of between 20-500 μs; and (d) Electroporating the macrophage with a second pulse phase, wherein the second pulse phase comprises a burst of pulses or a square pulse, wherein each pulse is between 50-225V, and wherein the second pulse phase lasts for a total period of 2000-50000 μs.

In one embodiment, the method may comprise the steps of:

(a) Providing a human monocyte;

(b) Culturing the human monocyte to produce a human macrophage;

(c) Polarising a human macrophage;

(d) Contacting the human polarized macrophage with genetic material;

(e) Electroporating the macrophage with a first pulse phase, wherein the first pulse phase comprises a burst of unipolar pulses or square pulse, wherein each pulse is between 750-1000V, and wherein the first pulse phase lasts for a total period of between 20-500 μs; and (f) Electroporating the macrophage with a second pulse phase, wherein the second pulse phase comprises a burst of pulses or a square pulse, wherein each pulse is between 50-225V, and wherein the second pulse phase lasts for a total period of 2000-50000 μs.

In an alternative embodiment, the method may further comprise a final step of polarising the transfected human macrophages, suitably into M1-like or M2-like transfected macrophages.

In one embodiment, the method may comprise the steps of:

(a) Contacting a human macrophage with genetic material;

(b) Electroporating the macrophage with a first pulse phase, wherein the first pulse phase comprises a burst of unipolar pulses or square pulse, wherein each pulse is between 750-1000V, and wherein the first pulse phase lasts for a total period of between 20-500 μs;

(c) Electroporating the macrophage with a second pulse phase, wherein the second pulse phase comprises a burst of pulses or a square pulse, wherein each pulse is between 50-225V, and wherein the second pulse phase lasts for a total period of 2000-50000 μs; and (d) Polarising the transfected human macrophage.

In one embodiment, the method may comprise the steps of:

(a) Providing a human monocyte;

(b) Culturing the human monocyte to produce a human macrophage;

(c) Contacting the human macrophage with genetic material;

(d) Electroporating the macrophage with a first pulse phase, wherein the first pulse phase comprises a burst of unipolar pulses or square pulse, wherein each pulse is between 750-1000V, and wherein the first pulse phase lasts for a total period of between 20-500 μs;

(e) Electroporating the macrophage with a second pulse phase, wherein the second pulse phase comprises a burst of pulses or a square pulse, wherein each pulse is between 50-225V, and wherein the second pulse phase lasts for a total period of 2000-50000 μs; and (f) Polarising the transfected human macrophage.

In one embodiment, the method comprises polarising a human macrophage into a M2-like phenotype.

In such an embodiment, suitably a human M2-like macrophage is produced. In such an embodiment, the method produces a transfected human M2-like macrophage.

Genetic Material

The invention relates to a method of transfecting human macrophages with genetic material so as to genetically modify the macrophages.

Suitably the genetic material may comprise any nucleic acid. Optionally the nucleic acid is heterologous to the macrophage. Suitably the genetic material may comprise a single-stranded nucleic acid or a double-stranded nucleic acid. Suitably the nucleic acid may be DNA or RNA. Suitably therefore, the genetic material may be DNA or RNA. In one embodiment, the nucleic acid is DNA. Suitably, therefore, in one embodiment, the genetic material is DNA. In one embodiment, the genetic material is an RNA such as messenger RNA (mRNA), small non-coding RNAs such as siRNA, shRNA and miRNA. The genetic material may be natural or may include modified nucleotides, such as LNA (locked nucleic acid).

Suitably the genetic material may be comprised on a vector. The vector may have any suitable architecture. Suitable vectors include plasmids, minicircles, cosmids, phage, viruses, yeast artificial chromosomes, bacterial artificial chromosomes, and the like. Suitably the genetic material is comprised on a plasmid. Suitable plasmids include pMAX, pRP, pRS, pSV, pCMV, pcDNA, pGEM. Suitably the plasmid comprises a size of between 3 kB-10 kB.

Alternatively, the genetic material may not be comprised on a vector and may be a free nucleic acid, such as an oligonucleotide. Suitably, the genetic material may be RNAi such as siRNA, shRNA, miRNA, or mRNA.

Suitably the genetic material encodes one or more genes of interest and/or one or more regulatory elements. Suitably the genetic material comprises a nucleic acid which encodes one or more genes of interest and/or one or more regulatory elements. Suitably the regulatory elements are operable to regulate gene expression, suitably of one or more genes of interest.

In one embodiment, the genetic material comprises a plasmid encoding one or more genes of interest and/or one or more regulatory elements. In one embodiment, the genetic material comprises a plasmid, wherein the plasmid comprises a nucleic acid encoding one or more genes of interest and/or one or more regulatory elements.

In one embodiment, the method may comprise the steps of:

(a) Contacting a human macrophage with genetic material, wherein the genetic material is a plasmid;
(b) Electroporating the macrophage with a first pulse phase, wherein the first pulse phase comprises a burst of unipolar pulses or square pulse, wherein each pulse is between 750-1000V, and wherein the first pulse phase lasts for a total period of between 20-500 μs; and
(c) Electroporating the macrophage with a second pulse phase, wherein the second pulse phase comprises a burst of pulses or a square pulse, wherein each pulse is between 50-225V, and wherein the second pulse phase lasts for a total period of 2000-50000 μs.

Suitably when the genetic material comprises more than one gene of interest and/or regulatory element of interest, the genetic material may comprise a linker sequence and/or internal ribosome entry site (IRES) for polycistronic expression, and/or more than one expression cassette. Suitably each expression cassette is operable to express one gene of interest, or two or more genes of interest and/or one or more regulatory elements. Suitably the genes of interest and/or one or more regulatory elements may comprise a linker sequence or IRES.

Suitably the genes of interest are endogenous or exogenous to the macrophages. Suitably the genes of interest may be homologous or heterologous to the macrophages.

In one embodiment, the genes of interest are heterologous to the macrophages.

In one embodiment, therefore, the genetic material comprises a plasmid encoding a heterologous gene of interest.

Suitably the regulatory elements are operable to regulate gene expression of one or more endogenous genes of interest within the macrophage genome, or one or more exogenous genes of interest encoded in the genetic material. Suitably, the regulatory elements are operable to regulate gene expression by upregulating or downregulating gene expression. Suitably, the regulatory elements may be operable to regulate gene expression by repressing gene expression or stimulating gene expression.

In one embodiment, the regulatory elements are operable to regulate gene expression by repressing endogenous gene expression or stimulating endogenous gene expression.

In one embodiment, therefore the genetic material comprises a plasmid encoding a regulatory element operable to repress or stimulate expression of an endogenous gene of interest.

Suitable genes of interest may encode one or more proteins of interest. Suitably the proteins of interest may be secreted by the macrophage. Alternatively, the proteins of interest may be expressed at the cell surface of the macrophage, in the cytoplasm of the macrophage, or in the nucleus of the macrophage. Suitably the genes of interest may encode one or more immunological or inflammatory proteins. Suitable genes of interest may encode proteins which have one or more of the following functions: phagocytic functions, fibrotic functions, paracrine functions, or restorative functions. Suitable genes of interest may encode immunological or inflammatory proteins which have one or more of the following functions: phagocytic functions, fibrotic functions, paracrine functions, or restorative functions.

For example, each gene of interest may encode one or more types of protein selected from the following: a b-cell differentiation factor, a b-cell growth factor, an angiogenesis factor, an adhesion factor, a cytokine, a chemokine, a growth factor, a transcription factor, a kinase, a phagocytosis factor, a cell survival factor and any fragments or combinations thereof.

Suitable regulatory elements include any nucleic acid sequence which can modify the expression of a gene. Suitable regulatory elements include promoters, operators, repressors, enhancers, silencers etc.

Suitably the genetic material comprises a promoter. Suitably a promoter directs transcription of an associated gene. Suitably the associated gene is a gene of interest. Suitably the promoter may be selected from any typical promoter used to modify human cells such as a mammalian promoter.

Suitably the promoter may be constitutive, repressible, or inducible. Suitably the promoter maybe inducible such that the rate of transcription of the associated gene increases in response to an inducing agent. Alternatively, the promoter may be repressible such that the rate of transcription of the associated gene decreases in response to a repressing agent. Suitably the inducing agent or the repressing agent may be a small molecule chemical or protein. Suitably the inducing agent or the repressing agent may be a drug.

In one embodiment, the promoter is constitutive. Suitably the promoter may be constitutive such that the rate of transcription of the associated gene is constant. In such an embodiment, the promoter is not regulated by an inducing agent or repressing agent. Suitable constitutive promoters can include, for example, SV40, CMV, UBC, EF1alpha, PGK, or CAGG. In one embodiment, the promoter is CMV.

Suitably the genetic material may be genomically integrated or may be cytoplasmic. Suitably the genetic material may be genomically integrated into the genome of the macrophage or may be cytoplasmic in the cytoplasm of the macrophage.

Suitably the genetic material is capable of being expressed in the macrophages. Suitably the genetic material is capable of being transiently or stably expressed in the macrophages. Suitably the genetic material may be capable of transient expression from a cytoplasmic nucleic acid. Alternatively, the genetic material may be capable of stable expression from a genomically integrated nucleic acid.

Suitably, in one embodiment, the genetic material may be capable of transient expression from an extrachromosomal nucleic acid, suitably a nucleic acid which is present in the nucleus and which may be described as an extrachromosomal nucleic acid. Suitably the extrachromosomal nucleic acid is comprised upon a vector, suitably a plasmid selected from those described above. Suitably therefore, in one embodiment, the genetic material comprises a plasmid, wherein the plasmid comprises a nucleic acid which is capable of transient expression in the macrophage.

In one embodiment, the genetic material comprises a plasmid encoding one or more genes of interest and/or one or more regulatory elements for transient expression in the macrophage. In one embodiment, the genetic material comprises a plasmid, wherein the plasmid comprises a nucleic acid encoding one or more genes of interest and/or one or more regulatory elements for transient expression in the macrophage. In one embodiment, the one or more regulatory elements may be transcribed in the nucleus from the extrachromosomal nucleic acid, and affect gene expression of endogenous genes.

Alternatively, in another embodiment, the genetic material may be capable of stable expression from a genomically integrated nucleic acid. Suitably the genomically integrated nucleic acid is comprised upon a vector, suitably a plasmid selected from those described above. Suitably, therefore, in one embodiment, the genetic material is a plasmid, wherein the plasmid comprises a nucleic acid which is capable of stable expression in the macrophage.

In one embodiment, the genetic material comprises a plasmid encoding one or more genes of interest and/or one or more regulatory elements for stable expression in the macrophage. In one embodiment, the genetic material comprises a plasmid, wherein the plasmid comprises a nucleic acid encoding one or more genes of interest and/or one or more regulatory elements for expression in the macrophage.

Suitably, the nucleic acid may be genomically integrated by one or more integration elements such as: transposons, Zn-finger nucleases, integrases, and recombinases. Suitably such integration elements may also be encoded by the genetic material, suitably such elements are also encoded upon a vector. Suitably the vector may be the same as the vector comprising the nucleic acid encoding one or more genes of interest and/or regulatory elements, or a different vector. Suitably, therefore, the genetic material may comprise one or more vectors encoding one or more genes of interest and/or one or more regulatory elements for stable expression in the macrophage, the one or more vectors further encoding one or more integration elements. Suitably, therefore, the genetic material may comprise one or more plasmids comprising one or more nucleic acids encoding one or more genes of interest and/or one or more regulatory elements for stable expression in the macrophage, the one or more plasmids further comprising one or more nucleic acids encoding one or more integration elements.

In one embodiment, the genetic material comprises a plasmid, wherein the plasmid comprises a nucleic acid encoding a heterologous gene of interest for transient expression in the macrophage.

In one embodiment, the genetic material comprises a plasmid, wherein the plasmid comprises a nucleic acid encoding a heterologous gene of interest and one or more nucleic acids encoding one or more integration elements for stable expression of the gene of interest in the macrophage.

Suitably the genetic material may further comprise one or more other expression elements such as: a terminator, an origin of replication, a start codon, a stop codon, ribosomal binding site, an internal ribosome entry site, 3'UTR regions, 5'UTR regions, a marker gene, a reporter gene, one or more cleavage sites, a tag etc.

Suitably the genetic material comprises a terminator or polyadenylation (pA) signal. Suitably the terminator may be selected from any suitable transcription terminator sequence. Suitably the terminator is a mammalian terminator. Suitable terminators include SV40, hGH, BGH, and rbGlob. In one embodiment, the genetic material comprises the terminator sequence SV40 late pA.

Suitably the genetic material may further comprise a marker gene. Suitably the marker gene may comprise a selectable marker gene. Suitably the selectable marker gene may be a positive or negative selectable marker gene. Suitably the marker gene may be an antibiotic resistance gene, a metabolic gene etc. Suitable antibiotic resistance genes include genes encoding resistance to ampicillin, kanamycin, chloramphenicol, tetracycline etc. In one embodiment, the genetic material comprises the antibiotic resistance gene AmpR.

Suitably the genetic material may further comprise a reporter gene. Suitably the reporter gene may indicate the level of expression of the transfected genetic material by the macrophage. Suitably the reporter may be flourescent. Suitably the reporter gene may be GFP, YFP, RFP, CFP, luciferase, etc. In some cases, the reporter gene may also be used as a marker. Suitably the reporter gene may be expressed together with the gene of interest to thereby indicate the level of expression of the gene of interest. Suitably the reporter gene may be expressed with the gene of interest as a fusion protein, or alternatively as a separate expression cassette in the same genetic material.

Suitably, the genetic material is a plasmid and the plasmid comprises one or more of the above regulatory and/or expression elements. Suitably the genetic material is a plasmid and the plasmid comprises: a promoter, a gene of interest, a terminator, and a marker.

In one embodiment, the genetic material is a plasmid and the plasmid comprises: a CMV promoter, a gene of interest, a SV40 late pA terminator, and a KanR antibiotic resistance gene.

In exemplary embodiments the gene of interest is a reporter gene to allow for detection of the level of expression of the transfected genetic material. However, the gene of interest may suitably be any gene or other regulatory element as explained above.

Transfection

The present invention relates to a method of transfecting macrophages. Suitably the method is non-viral.

Suitably the method may be a method of nucleofection of macrophages in which the genetic material enters the nucleus of the cell. Suitably, in such embodiments, the genetic material is an oligonucleotide, suitably selected from an oligonucleotide that can penetrate the nucleus of a cell, suitably RNAi such as siRNA, shRNA, or miRNA. Suitably such an oligonucleotide may be encoded by a nucleic acid upon a vector such as a plasmid.

Suitably the method of transfection is by electroporation. Typically, electroporation comprises the application of an electric current to cells by the use of electrodes. Typically, the cells are placed between the two electrodes before pulses of current are generated across the cells. The electrical pulses induce the temporary formation of pores in the cell membrane so that the genetic material can enter the cell through the pores by passive diffusion, or by active electrophoretic motion induced by the electric field if the genetic material is charged.

Suitably the electroporation steps may be performed by using any electroporator and programming the electroporator with the desired electroporation conditions. Suitably the electroporation steps are performed by using a cliniMACS electroporator (Miltenyi). Suitably the electroporation steps are performed by using a Lonza GMP Amaxa.

Suitably, prior to electroporation, the human macrophages are contacted with the genetic material. Suitably, the macrophages are contacted with the genetic material in solution. Suitably the solution is conductive. Suitably the solution is an electroporation solution. Suitably the electroporation solution is a buffer suitable for use with the chosen electroporator. Suitably, the buffer is Miltenyi buffer for use with the cliniMACS electroporator (Miltenyi).

Suitably the macrophages are present in the solution at a cell density of between $1\times10^5$ to $1\times10^9$ cells/mL, suitably between $1\times10^7$ to $1\times10^9$ cells/mL, suitably between $1\times10^8$ to $1\times10^9$ cells/mL, suitably $1\times10^5$ to $1\times10^8$ cells/mL, suitably between $5\times10^5$ to $8\times10^7$ cells/mL, suitably between $1\times10^6$ to $6\times10^7$ cells/mL, suitably between $5\times10^6$ to $5\times10^7$ cells/mL. In one embodiment, the macrophages are present in the solution at a cell density of at least $5\times10^7$ cells/mL. In one embodiment, the macrophages are present in solution at a cell density of at least $1.5\times10^8$ to about $2.0\times10^8$ cells/mL.

Suitably the macrophages are present in 100-1000 μL of solution. Suitably this is the typical volume of an electroporator cuvette. In one embodiment, the macrophages are present in 1000 μL of solution. Suitably therefore the number of macrophages electroporated is about $5\times10^6$ cells. Suitably, therefore, the number of macrophages electroporated is between about $7.5\times10^6$ and $10\times10^6$ cells.

Suitably the genetic material is present in the solution at a concentration of between 1 to 10 μg per $5\times10^6$ cells, suitably 2.5 to 10 μg per $5\times10^6$ cells, suitably at a concentration of between 3 to 9 μg per $5\times10^6$ cells, suitably at a concentration of between 4 to 8 μg per $5\times10^6$ cells, suitably at a concentration of between 5 to 7.5 μg per $5\times10^6$ cells. Suitably, the genetic material comprises a plasmid and is present in the solution at a concentration of between 2.5 to 10 μg per $5\times10^6$ cells, suitably at a concentration of between 3 to 9 μg per $5\times10^6$ cells, suitably at a concentration of between 4 to 8 μg per $5\times10^6$ cells, suitably at a concentration of between 5 to 7.5 μg per $5\times10^6$ cells.

Those skilled in the art may apply such ratios to the concentration of cells in the volume by routine calculation.

Suitably therefore, the method may comprise a step of (a) Contacting human macrophages with genetic material in solution, wherein the macrophages are present in the solution at a cell density of at least $5\times10^7$ cells/mL.

In one embodiment, the method may comprise the steps of:

(a) Contacting human macrophages with genetic material in solution, wherein the macrophages are present in the solution at a cell density of at least $5\times10^7$ cells/ml;

(b) Electroporating the macrophage with a first pulse phase, wherein the first pulse phase comprises a burst of unipolar pulses or square pulse, wherein each pulse is between 750-1000V, and wherein the first pulse phase lasts for a total period of between 20-500 μs; and (c) Electroporating the macrophage with a second pulse phase, wherein the second pulse phase comprises a burst of pulses or a square pulse, wherein each pulse is between 50-225V, and wherein the second pulse phase lasts for a total period of 2000-50000 μs.

Suitably therefore, the method may comprise a step of (a) Contacting human macrophages with genetic material in solution, wherein the genetic material comprises a plasmid and is present in the solution at a concentration of between 5 to 7.5 μg per $5\times10^6$ macrophage cells.

Suitably, the concentration of cells may be between about $1.5\times10^8$ to about $2.0\times10^8$ cells/mL.

In one embodiment, the method may comprise the steps of:

(a) Contacting human macrophages with genetic material in solution, wherein the genetic material is a plasmid and is present in the solution at a concentration of between 5 to 7.5 μg per $5\times10^6$ macrophage cells;

(b) Electroporating the macrophage with a first pulse phase, wherein the first pulse phase comprises a burst of unipolar pulses or square pulse, wherein each pulse is between 750-1000V, and wherein the first pulse phase lasts for a total period of between 20-500 μs; and (c) Electroporating the macrophage with a second pulse phase, wherein the second pulse phase comprises a burst of pulses or a square pulse, wherein each pulse is between 50-225V, and wherein the second pulse phase lasts for a total period of 2000-50000 μs.

Suitably the method of transfecting human macrophages is serum free. Suitably the method of transfecting human macrophages is xeno-molecule free. Suitably the method of transfecting human macrophages is GMP-compliant.

Suitably the transfection efficiency of the method is over 60%, over 65%, 70%, over 75%, over 80%, over 85%, suitably over 90%. Suitably the transfection efficiency of the method is at least over 85%.

Suitably, greater than 60%, greater than 65%, 70%, greater than 75%, greater than 80%, greater than 85%, greater than 90% of the transfected macrophage cells express the genetic material. Suitably, greater than 70%, greater than 75%, greater than 80%, greater than 85%, greater than 90% of the transfected macrophage cells express the or each gene of interest.

First and Second Pulse Phases

The present invention relates to a method of transfecting macrophages comprising two steps of electroporation. Suitably each step of electroporation is a pulse phase. Suitably each of the electroporation steps comprises electroporating the macrophages with a phase of one or more pulses, suitably pulses of electricity. Suitably each pulse phase comprises different parameters. Suitably each pulse phase comprises one or more pulses each having a defined form, voltage and period of time.

Suitably the method does not comprise any further steps of electroporation. Suitably the electroporation steps of the method consist of the two steps defined in the first aspect.

Suitably the first pulse phase comprises a burst of unipolar pulses or a square pulse. Suitably the second pulse phase comprises a burst of pulses or a square pulse. In one embodiment, the second pulse phase also comprises a burst of unipolar pulses.

Suitably a burst of pulses comprises a series of pulses, each lasting a short period of time. Suitably each pulse within a burst of pulses may last for between 3-40 μs, suitably between 3-10 μs, suitably between 5-8 μs. In one embodiment, each individual pulse within a burst of pulses lasts around 8 μs.

Suitably each pulse within a burst of pulses may be unipolar or bipolar. Suitably a unipolar pulse has one polarity, either positive or negative. Suitably a bipolar pulse has both polarities, positive and negative. Suitably a bipolar pulse may comprise a positive charge then a negative charge, or a negative charge then a positive charge.

Suitably each pulse within a burst of pulses has the same form. Suitably each pulse within a unipolar burst of pulses has the same polarity.

Suitably the burst of unipolar pulses may be positively charged, or negatively charged.

Suitably a square pulse comprises a single square pulse. Suitable the single square pulse lasts for the total period of time for the given pulse phase.

In one embodiment, the first pulse phase may comprise a burst of unipolar pulses, and the second pulse phase may comprise a burst of pulses.

In one embodiment, the first pulse phase may comprise a square pulse, and the second pulse phase may comprise a square pulse.

In one embodiment, the first pulse phase may comprise a burst of unipolar pulses, and the second pulse phase may comprise a square pulse.

In one embodiment, the first pulse phase may comprise a square pulse, and the second pulse phase may comprise a burst of pulses.

Suitably, in any embodiment, the burst of pulses is a unipolar burst of pulses. Suitably, if the first pulse phase comprises a burst of unipolar pulses, the second pulse phase also comprises a burst of unipolar pulses. Suitably both phases may comprise a burst of positively charged pulses.

Suitably the first pulse phase comprises pulses of between 750V-1000V, suitably between 800-1000V, suitably between 850-1000V, suitably between 900-1000V, suitably between 950-1000V. In one embodiment, the first pulse phase comprises pulses of about 950V. Suitably each pulse within the first pulse phase has the same voltage.

Suitably the first pulse phase is for a total period of time of between 20-500 μs, suitably between 50-450 μs, suitably between 50-400 μs, suitably between 50-350 μs, suitably between 50-300 μs, suitably between 50-250 μs, suitably between 50-200 μs, suitably between 75-175 μs, suitably between 100-150 μs. In one embodiment, the first pulse phase is for a total period of time of about 120 μs.

Suitably therefore, the first pulse phase may comprise a burst of unipolar pulses wherein each unipolar pulse is between 750-1000V and lasts for a period of between 5-8 μs. Suitably wherein the total first pulse phase lasts for between 20-500 μs.

Alternatively, the first pulse phase may comprise a square pulse, wherein the square pulse is between 750-1000V and lasts for the total first pulse phase of between 20-500 μs.

Suitably the second pulse phase comprises pulses of between 50-225V, suitably between 70-200V, suitably between 80-175V, suitably between 90-150V, suitably between 95-125V. In one embodiment, the second pulse phase comprises pulses of about 100-125V. Suitably each pulse within the second pulse phase has the same voltage.

Suitably the second pulse is for a total period of time of 2000-50000 μs, suitably between 5000-40000 μs, suitably between 10000-30000 μs, suitably between 11000-25000 μs, suitably between 12000-25000 μs, suitably between 11000-23000 μs, suitably between 12000-23000 μs. In one embodiment, the second pulse phase is for a total period of time of about 23000 μs.

Suitably therefore, the second pulse phase may comprise a burst of unipolar pulses wherein each unipolar pulse is between 50-225V and lasts for a period of between 5-8 μs. Suitably wherein the total first pulse phase lasts for between 2000-50000 μs.

Alternatively, the second pulse phase may comprise a square pulse, wherein the square pulse is between 50-225V and lasts for the total first pulse phase of between 2000-50000 μs.

In one embodiment, the method comprises the steps of:

(a) Contacting human macrophages with genetic material;

(b) Electroporating the macrophages with a first pulse phase, wherein the first pulse phase consists of a burst of unipolar pulses, wherein each pulse is of about 950V, and wherein the first pulse phase is for a total period of about 120 μs; and (c) Electroporating the macrophages with a second pulse phase, wherein the second pulse phase consists of a burst of unipolar pulses, wherein each pulse is between about 100-125V, and wherein the second pulse phase is for a total period of about 23000 μs.

Suitably in such an embodiment, each unipolar pulse lasts for about 6 μs.

Optionally, the method comprises a first pulse of 900V-1000V in 'burst-unipolar' mode with a burst length of 5-40 μsec and a total pulse length of 80-250 μsec.

Reduced IFN-β Expression

The method of the present invention may further comprise one or more steps which reduce expression of IFN-β by the transfected human macrophages. The invention therefore further provides transfected human macrophages comprising a heterologous nucleic acid, and having reduced IFN-β expression.

Advantageously, reduced IFN-β expression means that the transfected macrophage is able to maintain function and is less pro-inflammatory.

In one embodiment, the expression of IFN-β is reduced by repression of the STING pathway in the transfected macrophages. In one embodiment, there is provided a transfected human macrophage comprising a heterologous nucleic acid, wherein the macrophage has a repressed STING pathway. Repression of the STING pathway is described in more detail below.

In an alternative embodiment, the expression of IFN-β is reduced by polarising the transfected macrophages. In one embodiment, there is provided a transfected human macrophage comprising a heterologous nucleic acid, wherein the macrophage is polarized.

Suitably these alternative methods discovered by the inventors each lead to reduced expression of IFN-β in the transfected macrophages. Suitably both of these methods may be combined.

Suitably the expression of IFN-β is reduced by at least 10%, at least 15%, at least 20%, at least 25%, at least 30%, at least 35%, at least 40%, at least 45%, at least 50%, at least 55%, at least 60%, at least 65%, at least 70%, at least 75% relative to a transfected macrophage that does not have a repressed STING pathway and/or which is not polarized.

Suitably repression of the STING pathway may be accomplished by the use of a STING pathway inhibitor.

Suitably, the method of the present invention may further comprise the use of a STING pathway inhibitor. Suitably the STING pathway inhibitor represses the STING pathway. Suitably repression of the STING pathway prevents activation of interferon secretion.

Suitably the STING pathway inhibitor may be added during the method of transfecting the macrophages. Suitably the STING pathway inhibitor is added after the electroporation steps. Suitably therefore the method may comprise a step of contacting the macrophages with a STING pathway inhibitor, suitably contacting the transfected macrophages with a STING pathway inhibitor.

In one embodiment, the method comprises the steps of:

(a) Contacting a human macrophage with genetic material;

(b) Electroporating the macrophage with a first pulse phase, wherein the first pulse phase comprises a burst of unipolar pulses or a square pulse, wherein each pulse is between 750-1000V, and wherein the first pulse phase lasts for a total period of between 20-500 μs;

(c) Electroporating the macrophage with a second pulse phase, wherein the second pulse phase comprises a burst of pulses or a square pulse, wherein each pulse is between 50-225V, and wherein the second pulse phase lasts for a total period of 2000-50000 μs; and (d) Contacting the macrophage with a STING inhibitor.

Suitably the STING pathway inhibitor is a small molecule. Suitably the STING inhibitor may be selected from BX-795, H-151, Amlexanox, MRT67307, for example. In one embodiment, the STING pathway inhibitor is BX-795.

Suitably the STING pathway inhibitor is used as a solution. Suitably as a solution at a concentration of between 2.5-10 μM, suitably between 6-9 μM, suitably between 7-8 μM, suitably 8 μM.

Alternatively, a nucleic acid encoding a STING pathway inhibitor may be transfected into the macrophages. Suitably the genetic material may comprise a nucleic acid encoding a STING pathway inhibitor. Suitably in addition to the gene of interest and/or regulatory elements discussed herein above. Suitably the transfected macrophages express the STING pathway inhibitor.

Suitably therefore, in one embodiment, the transfected macrophages of the invention comprise a heterologous nucleic acid encoding a STING pathway inhibitor.

Suitably, whether the STING pathway inhibitor is contacted with the macrophages or if it is expressed within the macrophages, the transfected macrophages comprise repression of the STING pathway, which is typically activated by transfected nucleic acids. Suitably repression occurs by inhibiting or repressing one or more elements of the STING pathway, and/or one or more elements controlling the STING pathway. Suitably, such inhibition or repression of the STING pathway may comprise inhibiting or blocking the activation of the STING pathway, suitably therefore inhibition or repression of the STING pathway may comprise non-activation of the STING pathway.

Suitably the STING pathway inhibitor inhibits a kinase in the STING pathway. Suitably the STING pathway inhibitor binds to and inhibits a kinase in the STING pathway. Suitably the STING pathway inhibitor inhibits an IKK-related kinase such as TANK-binding kinase 1 (TBK1) and IKKε. Suitably the STING pathway inhibitor inhibits activation of IRF3. Suitably the STING pathway inhibitor thereby inhibits expression of IFN-β. Suitably the STING pathway inhibitor inhibits activation of IRF3 by preventing phosphorylation of IRF3. Suitably the STING pathway inhibitor inhibits activation of IRF3 by preventing phosphorylation of IRF3 by a kinase. Suitably the STING pathway inhibitor inhibits activation of IRF3 by preventing phosphorylation of IRF3 by TANK-binding kinase 1. Suitably in such an embodiment, the STING pathway inhibitor is BX-795.

Suitably the STING pathway may be considered as repressed or inhibited. Suitably the STING pathway is repressed or inhibited relative to a transfected macrophage that is not contacted with, or does not comprise a heterologous nucleic acid encoding, a STING pathway inhibitor. Suitably the STING pathway is repressed by at least 10%, at least 15%, at least 20%, at least 25%, at least 30%, at least 35%, at least 40%, at least 45%, at least 50%, at least 55%, at least 60%, at least 65%, at least 70%, at least 75% relative to a transfected macrophage that is not contacted with, or does not comprise a heterologous nucleic acid encoding, a STING pathway inhibitor.

Suitably the phosphorylation of IRF3 is reduced by at least 10%, at least 15%, at least 20%, at least 25%, at least 30%, at least 35%, at least 40%, at least 45%, at least 50%, at least 55%, at least 60%, at least 65%, at least 70%, at least 75% relative to a transfected macrophage that is not contacted with, or does not comprise a heterologous nucleic acid encoding, a STING pathway inhibitor. Suitably in such an embodiment, the STING pathway inhibitor is BX-795.

Suitably the expression of IFN-β is reduced by at least 10%, at least 15%, at least 20%, at least 25%, at least 30%, at least 35%, at least 40%, at least 45, at least 50%, at least 55%, at least 60%, at least 65%, at least 70%, at least 75% relative to a transfected macrophage that is not contacted with, or does not comprise a heterologous nucleic acid encoding, a STING pathway inhibitor. Suitably in such an embodiment, the STING pathway inhibitor is BX-795.

Suitably, STING inhibition may be achieved by contacting the macrophage after transfection with anti-inflammatory cytokines. Notably, the transfected macrophage may be contacted by either IL10, or IL4 and IL13 (IL4+IL13).

The transfected macrophages may be contacted with these anti-inflammatory cytokines (IL10, or IL4/IL13) for a period of about 2 hours to about 48 hours, suitably 4 hours to 40 hours, suitably 12 to 24 hours, optionally around 16 hours.

The transfected macrophages may be contacted with these anti-inflammatory cytokines (IL10 or IL4/IL13) at a concentration of between 2 ng/ml and 200 ng/ml, suitably between 5 ng/ml and 150 ng/ml, suitably between 10 ng/ml to 100 ng/ml, suitably between 15 ng/ml to 75 ng/ml, suitably between 20 ng/ml to 50 ng/ml.

Alternatively, the method of the present invention may further comprise polarization of the macrophages. Suitably polarization prevents activation of interferon secretion. Suitably polarization of the macrophages may be into the M1-like or M2-like phenotypes. Suitably this is achieved by contacting the macrophages with various polarization factors as explained elsewhere herein. Suitably polarization of the macrophages may take place before or after transfection.

In one embodiment, polarization takes place after transfection of the macrophages.

Suitably, the transfected macrophages may be polarized into the M1-like phenotype by contacting with the factors: IFNγ or IFNγ+LPS.

Suitably, the transfected macrophages may be polarized into the M2-like phenotype by contacting with the factors: IL4+IL13, or IL10.

The inventors have found that interferon secretion is reduced the most when the macrophages are polarized with the M2 polarization factors IL4 and IL13. Therefore, in one embodiment, the transfected macrophages are polarized into the M2-like phenotype by contacting with IL4+IL13.

In one embodiment, the method comprises the steps of:

(a) Contacting a human macrophage with genetic material;
(b) Electroporating the macrophage with a first pulse phase, wherein the first pulse phase comprises a burst of unipolar pulses or a square pulse, wherein each pulse is between 750-1000V, and wherein the first pulse phase lasts for a total period of between 20-500 μs;
(c) Electroporating the macrophage with a second pulse phase, wherein the second pulse phase comprises a burst of pulses or a square pulse, wherein each pulse is between 50-225V, and wherein the second pulse phase lasts for a total period of 2000-50000 μs; and
(d) Polarising the transfected macrophage.

In one embodiment, the method comprises the steps of:

(a) Contacting a human macrophage with genetic material;
(b) Electroporating the macrophage with a first pulse phase, wherein the first pulse phase comprises a burst of unipolar pulses or a square pulse, wherein each pulse is between 750-1000V, and wherein the first pulse phase lasts for a total period of between 20-500 μs;
(c) Electroporating the macrophage with a second pulse phase, wherein the second pulse phase comprises a burst of pulses or a square pulse, wherein each pulse is between 50-225V, and wherein the second pulse phase lasts for a total period of 2000-50000 μs; and
(d) Polarising the transfected macrophage by contacting it with an M1 or M2 polarization factor.

In one embodiment, the method comprises the steps of:

(a) Contacting a human macrophage with genetic material;
(b) Electroporating the macrophage with a first pulse phase, wherein the first pulse phase comprises a burst of unipolar pulses or a square pulse, wherein each pulse is between 750-1000V, and wherein the first pulse phase lasts for a total period of between 20-500 μs;
(c) Electroporating the macrophage with a second pulse phase, wherein the second pulse phase comprises a burst of pulses or a square pulse, wherein each pulse is between 50-225V, and wherein the second pulse phase lasts for a total period of 2000-50000 μs; and
(d) Polarising the transfected macrophage by contacting it with IL4 and IL13.

Transfected Human Macrophages

The present invention further relates to transfected macrophages produced by the method, which may be used in cell therapy, and generally to transfected human macrophages comprising a heterologous nucleic acid, wherein the macrophages have a repressed STING pathway. The invention further relates to a population of transfected macrophages produced by the method, and to a population of transfected human macrophages having a viability of over 60%.

Suitably the macrophages may also be known as modified macrophages, because suitably the macrophages are modified. Suitably the macrophages are genetically modified. Suitably the macrophages are modified with genetic material, suitably by the introduction of genetic material as per the method of the invention.

Suitably the macrophages may be stably transfected or transiently transfected as explained above. Suitably, therefore, the macrophages may be stably modified or transiently modified.

Suitably the macrophages may be modified to express one or more genes of interest. Alternatively, the macrophages may be modified to repress one or more genes of interest. Suitably the macrophages may be modified to upregulate expression of one or more genes of interest. Suitably the macrophages may be modified to downregulate expression of one or more genes of interest.

In one embodiment, the macrophages are modified to express or upregulate expression of a gene of interest, suitably a gene encoding an advantageous protein, such as a therapeutic protein.

In one embodiment, the macrophages are modified to repress or downregulate expression of a gene of interest, suitably a gene encoding a deleterious protein, such as a pathogenic protein.

Suitably the one or more genes of interest, and/or one or more regulatory elements for controlling expression of one or more genes of interest, are encoded in the genetic material which is transfected into the macrophages using the method of the invention. Suitable genes of interest are described hereinabove.

Suitably, the transfected macrophages are manufactured to a GMP-compliant standard. Suitably therefore the transfected macrophages and populations thereof are GMP-compliant.

Suitably the transfected macrophages produced by the method of the invention are novel by virtue of the method. Suitably therefore, the invention provides a transfected macrophage produced by the method, or a population of such transfected macrophages produced by the method.

Suitably the transfected macrophages produced by the method of the invention have a high viability. Advantageously, the viability of the transfected macrophages produced by the method of the invention is much higher than previous attempts to transfect human macrophages.

Suitably, therefore, the invention further provides a population of transfected human macrophages, wherein the viability of the population is at least 60%.

Suitably the transfected macrophages have a viability of over 60%, over 70%, over 80%, over 85%, over 90%, over 95%. In one embodiment, the transfected macrophages produced by the method of the invention have a viability of at least 80%. Suitably the transfected macrophages produced by the method of the invention also have a high transfection rate. Advantageously, the transfection efficiency of the method of the invention is much higher than previous attempts to transfect macrophages by electroporation.

Suitably the method of the invention has a transfection efficiency of over 60%, 70%, over 80%, over 90%, over 95%.

Suitably the population of transfected macrophages has a transfection rate of over 60%, over 70%, over 80%, over 90%, over 95%.

In one embodiment, the population of transfected macrophages has a viability of at least 60% and a transfection rate of at least 60%.

Suitably the invention further provides a transfected human macrophage comprising a heterologous nucleic acid, wherein the transfected human macrophage has a repressed STING pathway.

Suitably, as explained above, the transfected human macrophage may have a repressed STING pathway and/or may be polarized. Suitably, as explained above, the transfected human macrophage may further have reduced expression of IFN-β.

Suitably the repressed STING pathway is described herein above. Suitably the population of transfected human macrophages described herein may also comprise a repressed STING pathway. Suitably the repressed STING pathway may be as a result of contacting the transfected macrophages with a STING pathway inhibitor, or alternatively as result of comprising a nucleic acid encoding a STING pathway inhibitor.

Suitably the polarization of macrophages is described hereinabove. Suitably the population of transfected human macrophages described herein may also comprise a population of transfected polarized macrophages. Suitably the polarized macrophages may be as a result of contacting the transfected macrophages with one or more polarization factors.

Suitably the macrophages within the population of transfected human macrophages comprise a heterologous nucleic acid. Suitably the heterologous nucleic acid within the transfected macrophage or a population thereof comprises a gene of interest and/or a regulatory element. Suitably such genes and/or regulatory elements are described elsewhere herein. Suitably the heterologous nucleic acid is non-viral.

Suitably the method of transfection is non-viral. Suitably therefore the heterologous nucleic acid is not a virus, and suitably the transfected macrophage is non-virally transfected.

Suitably the heterologous nucleic acid within the transfected macrophage or a population thereof may encode a STING pathway inhibitor as explained above. Suitably in addition to a gene of interest and/or a regulatory element.

Suitably the transfected macrophages may be cryopreserved. Suitably by any cryopreservation method. For example, cooling in growth medium or serum solution containing 5-20% DMSO for cryopreservation.

Suitably the transfected macrophages or a population thereof according to the invention may be supplied in a container suitable for further use. In a further aspect of the invention there is provided a culture bag or expansion bag comprising a transfected macrophage according to a second or third aspect of the present invention, or a population of transfected macrophages according to the fourth or fifth aspect of the present invention.

Medical Uses

The present invention further relates to transfected human macrophages, and populations thereof, for use as a medicament. Suitably any references to transfected macrophages below also include a population of transfected macrophages.

Suitably, the transfected macrophages are for use in the treatment of a subject having a disease or suspected of having a disease.

Suitably, the transfected macrophages are for use in therapy.

Suitably, the transfected macrophages are for use in the treatment of a subject having a disease or suspected of having a disease by cell therapy. Suitably the transfected macrophages may be for use in the treatment of a subject having a disease by immunotherapy.

Suitably the subject may be regarded as a patient. Suitably the subject may be a human or animal, suitably the subject is a human. Suitably the subject may be a child or an adult, suitably the subject is an adult.

Suitably the subject may be in need of treatment. Suitably therefore the subject may have a disease, or be at risk of developing a disease. Suitably the subject may display one or more symptoms of a disease.

Suitably the subject may have, or be at risk of developing, a liver disease or injury as defined hereinabove.

Suitably the subject may satisfy certain risk factors associated with liver disease or injury, for example: alcoholism, drug abuse, obesity, an autoimmune disorder, metabolic syndrome, taking certain medications, exposure to toxic chemicals/microorganisms.

Suitably the subject may have symptoms of a disease. Suitably the subject may have symptoms associated with a liver disease or injury.

Suitably the subject may have one or more of the following symptoms: nail clubbing, palmar erythema, angiomata, gynaecomastia, testicular atrophy, anaemia, caput medusae, drowsiness, hyperventilation, asterixis, jaundice, ascites, leukonychia, peripheral edema, bruising, respiratory alkalosis, liver enlargement, dupuytren's contracture, parotid enlargement, peripheral neuropathy, and kayser-fleisher rings, for example.

Suitably the medical use of the transfected macrophages will depend on the genetic material with which they are transfected using the method of the invention. Suitably therefore, the transfected macrophages may be for use in the treatment of any disease.

Suitably the disease may be acute, chronic, or acute-on-chronic.

Suitably an acute disease or injury may be classed as a disease or injury with an onset of less than 24 weeks from cause. Suitably a chronic disease may be classed as a disease or injury which has persisted for more than 6 months. Suitably an acute-on chronic disease may be classed as a disease or injury with an onset of less than 24 weeks from cause in a patient that already has a chronic disease that has persisted for more than 6 months.

Suitably the transfected macrophages may be for use in the treatment of fibrotic and or inflammatory diseases, suitably for use in the treatment of diseases which involve fibrosis and/or inflammation. Suitably the transfected macrophages may be for use in the treatment of a disease by reducing fibrosis and/or inflammation. Suitably the fibrotic disease or inflammatory disease may be acute, chronic or acute-on-chronic.

Suitably the transfected macrophages may be for use in the treatment of any liver disease, kidney disease, lung disease, or muscle disease. Suitably the transfected macrophages may be for use in the treatment of any fibrotic disease or inflammatory disease in the liver, kidney, lung, or muscle. Suitably the transfected macrophages may be for use in the treatment of any fibrotic disease, or inflammatory disease in the liver.

Suitably the transfected macrophages may be for use in the treatment of fibrotic liver disease, fibrotic kidney disease, fibrotic lung disease, or fibrotic muscle disease. Suitably the transfected macrophages may be for use in the treatment of an inflammatory liver disease, inflammatory kidney disease, inflammatory lung disease, or inflammatory muscle disease. Suitably the transfected macrophages may be for use in the treatment of liver diseases, kidney diseases, lung diseases, or muscle diseases by reducing fibrosis and/or by reducing inflammation. Suitably the transfected macrophages may be for use in the treatment of fibrotic liver diseases and/or inflammatory liver diseases. Suitably the transfected macrophages may be for use in the treatment of liver diseases by reducing fibrosis and/or by reducing inflammation.

Suitable liver diseases include: chronic liver disease, acute liver disease, acute-on-chronic liver disease, Alagille Syndrome, Alcohol-Related Liver Disease, acute fatty liver of pregnancy, Alpha-1 Antitrypsin Deficiency, Autoimmune Hepatitis, Benign Liver Tumours, Biliary Atresia, Budd Chiari syndrome, Cirrhosis, Crigler-Najjar Syndrome, Cystic fibrosis related liver disease, Gallstones, Galactosemia, Gilbert Syndrome, Hemochromatosis, Hepatic Encephalopathy, Hepatitis A, Hepatitis B, Hepatitis C, Hepatitis E, Hepatorenal Syndrome, Intrahepatic Cholestasis of Pregnancy (ICP), Lysosomal Acid Lipase Deficiency (LAL-D), Liver Cysts, Liver abscesses, Liver Cancer, Newborn Jaundice, Non-Alcoholic Fatty Liver Disease, Non-Alcoholic Steatohepatitis, Primary Biliary Cholangitis (PBC), *Porphyria*, Portal hypertension, Primary Sclerosing Cholangitis (PSC), Progressive Familial Intrahepatic Cholestasis (PFIC), Reye Syndrome, Type I Glycogen Storage Disease, Wilson Disease.

Suitably lung diseases include: chronic lung disease, acute lung disease, acute-on-chronic lung disease, asthma, COPD, pneumonia, emphysema, pulmonary fibrosis, lung cancer, mesothelioma, cystic fibrosis, tuberculosis, respiratory infections, pulmonary edema, bronchitis, pulmonary embolism, pulmonary hypertension, sarcoidosis, interstitial lung disease, Langerhans cell histiocytosis, bronchiolitis obliterans, post inflammatory pulmonary fibrosis, pulmonary alveolar proteinosis, idiopathic pulmonary hemosiderosis, pulmonary alveolar microlithiasis, idiopathic interstitial pneumonia, idiopathic pulmonary fibrosis, acute interstitial pneumonitis, cryptogenic organising pneumonia, desquamative interstitial pneumonia, lymphangioleiomyomatosis, neuroendocrine cell hyperplasia, pulmonary interstitial glycogenosis, alveolar dysplasia, rheumatoid lung disease, cytokine release syndrome (CRS)-induced acute respiratory distress syndrome (ARDS), secondary hemophagocytic lymphohistiocytosis (sHLH), and COVID-induced fibrosis.

Suitable kidney diseases include: chronic kidney disease, acute kidney disease, acute-on-chronic kidney disease, Abderhalden-Kaufmann-Lignac syndrome (Nephropathic Cystinosis), Acute Kidney Failure/Acute Kidney Injury, Acute Lobar Nephronia, Acute Phosphate Nephropathy, Acute Tubular Necrosis, Adenine Phosphoribosyltransferase Deficiency, Apparent Mineralocorticoid Excess Syndrome, Arteriovenous Malformations and Fistulas of the Urologic Tract, Autosomal Dominant Hypocalcemia, Bardet-Biedl Syndrome, Bartter Syndrome, Beer Potomania, Beeturia, β-Thalassemia Renal Disease, Bile Cast Nephropathy, Birt-Hogg-Dube Syndrome, Clq Nephropathy, C3 Glomerulopathy C3 Glomerulopathy with Monoclonal Gammopathy, C4 Glomerulopathy, CAKUT (Congenital Anomalies of the Kidney and Urologic Tract), Capillary Leak Syndrome, Cardiorenal syndrome, CFHR5 nephropathy, Charcot-Marie-Tooth Disease with Glomerulopathy, Churg-Strauss syndrome, Chyluria, Ciliopathy, Cold Diuresis, Collagenofibrotic Glomerulopathy, Collapsing Glomerulopathy, Congenital Anomalies of the Kidney and Urinary Tract (CAKUT), Congenital Nephrotic Syndrome, Congestive Renal Failure, Conorenal syndrome (Mainzer-Saldino Syndrome or Saldino-Mainzer Disease), Contrast Nephropathy, Cortical Necrosis, Cryocrystalglobulinemia, Cryoglobuinemia, Crystal-Storing Histiocytosis, Cystinuria, Dense Deposit Disease (MPGN Type 2), Dent Disease (X-linked Recessive Nephrolithiasis), Dialysis Disequilibrium Syndrome, Diabetes and Diabetic Kidney Disease, Diuresis, Drug and substance induced kidney disease, EAST syndrome, Ectopic Kidney, Erdheim-Chester Disease, Fabry's Disease, Familial Hypocalciuric Hypercalcemia, Fanconi Syndrome, Fraser syndrome, Fibrillary Glomerulonephritis and Immunotactoid Glomerulopathy, Fraley syndrome, Hypervolemia, Focal Segmental Glomerulosclerosis, Focal Glomerulosclerosis, Galloway Mowat syndrome, Hypertension, Gitelman Syndrome, Glomerular Diseases, Glomerular Tubular Reflux, Glycosuria, Goodpasture Syndrome, HANAC Syndrome, Heat Stress Nephropathy, Hemolytic Uremic Syndrome (HUS), Atypical Hemolytic Uremic Syndrome (aHUS), Hemophagocytic Syndrome, Hemorrhagic Cystitis, Nephropathis Epidemica), Hemosiderinuria, Hemosiderosis related to Paroxysmal Nocturnal Hemoglobinuria and Hemolytic Anemia, Hepatic Glomerulopathy, Hepatic Veno-Occlusive Disease, Sinusoidal Obstruction Syndrome, Hepatitis C-Associated Renal Disease, Hepatocyte Nuclear Factor 1β-Associated Kidney Disease, Hepatorenal Syndrome, HNF1B-related Autosomal Dominant Tubulointerstitial Kidney Disease, Horseshoe Kidney (Renal Fusion), Hunner's Ulcer, Hydrophilic Polymer Emboli, Hyperaldosteronism, Hypercalcemia, Hyperkalemia, Hypermagnesemia, Hypernatremia, Hyperoxaluria, Hyperphosphatemia, Hypocalcemia, Hypocomplementemic Urticarial Vasculitic Syndrome, Hypokalemia-induced renal dysfunction, Hypomagnesemia, Hyponatremia, Hypophosphatemia, Interstitial Nephritis, Infection induced kidney disease, Ivemark's syndrome, Joubert Syndrome, Kidney Stones, Nephrolithiasis, Kidney cancer, Lecithin Cholesterol Acyltransferase Deficiency (LCAT Deficiency), Liddle Syndrome, Lightwood-Albright Syndrome, Lipoprotein Glomerulopathy, Lupus, Systemic Lupus Erythematosis, Lysinuric Protein Intolerance, Lysozyme Nephropathy, Malignancy-Associated Renal Disease, Malakoplakia, McKittrick-Wheelock Syndrome, Meatal Stenosis, Medullary Cystic Kidney Disease, Urolodulin-Associated Nephropathy, Juvenile Hyperuricemic Nephropathy Type 1, Medullary Sponge Kidney, MELAS Syndrome, Membranoproliferative Glomerulonephritis, Membranous Nephropathy, MesoAmerican Nephropathy, Metabolic Acidosis, Metabolic Alkalosis, Microscopic Polyangiitis, Milk-alkalai syndrome, Dysproteinemia, MUC1 Nephropathy, Multicystic dysplastic kidney, Multiple Myeloma, Myeloproliferative Neoplasms and Glomerulopathy, Nail-patella Syndrome, NARP Syndrome, Nephrocalcinosis, Nephrocystin-1 Gene Deletions and ESRD, Nephrogenic Systemic Fibrosis, Nephronophthisis due to Nephrocystin-1 Gene Deletions, Nephroptosis (Floating Kidney, Renal Ptosis), Nephrotic Syndrome, Nodular Glomerulosclerosis, Nutcracker syndrome, Oligomeganephronia, Orotic Aciduria, Oxalate Nephropathy, Page Kidney, Papillary Necrosis, Papillorenal Syndrome (Renal-Coloboma Syndrome, Isolated Renal Hypoplasia), The Peritoneal-Renal Syndrome, POEMS Syndrome, Podocyte Infolding Glomerulopathy, Post-infectious Glomerulonephritis, Polyarteritis Nodosa, Polycystic Kidney Disease, Posterior Urethral Valves, Post-Obstructive Diuresis, Proliferative Glomerulonephritis with Monoclonal IgG Deposits (Nasr Disease), Proteinuria (Protein in Urine), Pseudohyperaldosteronism, Pseudohypobicarbonatemia, Pseudohypoparathyroidism, Pulmonary-Renal Syndrome, Pyelonephritis (Kidney Infection), Pyonephrosis, Reflux Nephropathy, Rapidly Progressive Glomerulonephritis, Renal Abscess, Peripnephric Abscess, Renal Agenesis, Renal Arcuate Vein Microthrombi-Associated Acute Kidney Injury, Renal Artery Aneurysm, Renal Artery Stenosis, Renal Cell Cancer, Renal Cyst, Renal Infarction, Renal Osteodystrophy, Renal Tubular Acidosis, Retroperitoneal Fibrosis, Rhabdomyolysis, Rheumatoid Arthritis-Associated Renal Disease, Sarcoidosis Renal Disease, Salt Wasting, Scleroderma Renal Crisis, Serpentine Fibula-Polycystic Kidney Syndrome, Exner Syndrome, Sickle Cell Nephropathy, TAFRO Syndrome, Tea and Toast Hyponatremia, Thin Basement Membrane Disease, Benign Familial Hematuria, Thrombotic Microangiopathy Associated with Monoclonal Gammopathy, Trench Nephritis, Trigonitis, Tuberculosis, Genitourinary, Tuberous Sclerosis, Tubular Dysgenesis, Immune Complex Tubulointerstitial Nephritis Due to Autoantibodies to the Proximal Tubule Brush Border, Tumour Lysis Syndrome, Uremia, Uremic Optic Neuropathy, Ureteritis Cystica, Ureterocele, Urethral Caruncle, Urethral Stricture, Urinary Tract Infection, Urogenital Fistula, Uromodulin-Associated Kidney Disease, Vasomotor Nephropathy, Vesicointestinal Fistula, Vesicoureteral Reflux, VGEF Inhibition and Renal Thrombotic Microangiopathy, viral induced kidney disease, Von Hippel-Lindau Disease, Waldenstrom's Macroglobulinemic Glomerulonephritis, Wegener's Granulomatosis, Granulomatosis with Polyangiitis, Wunderlich syndrome, Zellweger Syndrome, Cerebrohepatorenal Syndrome.

Suitable muscle diseases include: chronic muscle diseases, acute muscle diseases, acute-on-chronic muscle diseases, muscular dystrophies (e.g. Duchenne muscular dystrophy, limb girdle muscular dystrophies), idiopathic inflammatory myopathies (e.g. Dermatomyositis, Polymyositis), Myasthenia gravis, Amyotrophic Lateral Syndrome, Mitochondrial myopathies, Rhabdomyolysis, Fibromyalgia, sprains and strains, and Muscle tumours, such as leiomyomas, rhabdomyomas, and rhabdomyosarcomas.

Suitably, the transfected macrophages may be for use in the treatment of acute, chronic or acute-on chronic liver disease.

Suitably a chronic liver disease/injury may be selected from the following: hepatitis C; hepatitis B; alcohol related liver disease; non-alcoholic fatty liver disease; cryptogenic cirrhosis; Wilson's disease; autoimmune hepatitis; cholangitis; hemochromatosis; and alpha-1-antitrypsin deficiency.

Suitably an acute liver disease/injury may be caused by the following: excessive alcohol consumption; adverse reaction to medications; poisoning for example by food, chemicals, toxins; infection with microorganisms such as cytomegalovirus, Epstein Barr virus, yellow fever; acute fatty liver of pregnancy; and drug overdose, for example acetaminophen overdose (APAP).

In one embodiment, the transfected macrophages are for use in the treatment of a fibrotic disease, suitably a fibrotic liver disease. Suitably the fibrotic liver disease may be acute, chronic or acute-on chronic. In one embodiment, the transfected macrophages are for use in the treatment of acute-on-chronic liver disease.

In one embodiment, the transfected macrophages are for use in the treatment of liver cirrhosis. In one embodiment, the transfected macrophages are for use in the treatment of APAP overdose.

Suitably the transfected macrophages may be formulated into a pharmaceutical composition. Suitably the composition is suitable for administration to a subject. Suitably the composition is a liquid. Suitably the composition is an infusible liquid.

In a further aspect of the invention there is provided a composition comprising the transfected human macrophages of the invention or a population thereof. In one embodiment, the composition is a pharmaceutical composition.

Suitably any of the medical uses defined herein in relation to the transfected human macrophages or populations thereof may equally apply to the compositions.

Suitably such formulations or compositions may comprise one or more acceptable carriers such as excipients or diluents, for example, water, saline, and dextrose. Suitably the pharmaceutical composition may further comprise binders, fillers, preservatives, stabilizing agents, emulsifiers, and/or buffers. Suitably the macrophages are formulated with the one or more acceptable carriers. It will be recognized by one of skill in the art that the form and character of the pharmaceutically acceptable carrier or diluent is dictated by the amount of active ingredient with which it is to be combined, the route of administration and other well-known variables.

Suitably the formulation or composition may comprise pharmaceutically acceptable carriers, including, e.g., water, ion exchangers, alumina, aluminium stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol, and wool fat.

Suitably the formulation or composition may include sterile aqueous solutions. Aqueous carriers include, e.g. water, aqueous solutions or suspensions, including saline and buffered media.

Suitably pharmaceutically acceptable carriers include, but are not limited to, 0.01-0.1 M and preferably 0.05 M phosphate buffer or 0.8% saline. Other common parenteral carriers include sodium phosphate solutions, Ringer's dextrose, dextrose and sodium chloride, and lactated Ringer's. Intravenous carriers include fluid and nutrient replenishers, electrolyte replenishers, such as those based on Ringer's dextrose, and the like. Preservatives and other additives may also be present such as, for example, antioxidants, chelating agents, and the like.

Suitably, formulations or compositions for injectable use may include sterile aqueous solutions (where water soluble) or dispersions and sterile powders for the extemporaneous preparation of sterile injectable solutions or dispersions. In such cases, the composition must be sterile and should be fluid to the extent that easy syringability exists. It should be stable for a determined shelf-life under the conditions of manufacture and storage. Suitably, the carrier can be a solvent or dispersion medium containing, for example, water, polyol (e.g. glycerol, propylene glycol, and liquid polyethylene glycol, and the like), and suitable mixtures thereof.

Suitable excipients may include: buffers such as PBS buffer or PBS buffer with 0.5% HAS (human albumin serum); saline such as 0.9% saline or 0.9% saline with 0.5% HAS.

Suitably the formulation or composition may further comprise additives, such as antioxidants, or preservatives, for example. Suitably the formulation or composition may further comprise DMSO, suitably 5-10% DMSO if the modified macrophage is to be cryopreserved.

Suitably the transfected human macrophages of the invention may be combined with a second therapeutic agent. Suitably therefore the transfected human macrophages of the invention may be formulated into a medicament with a second therapeutic agent.

Suitably the transfected macrophages are for administration to a subject by any route. Suitably the transfected macrophages are for administration to a subject by infusion. Suitably the macrophages are for administration to a subject parenterally, suitably intravenously. Suitably the macrophages are for administration to a subject by injection or infusion. Suitably the transfected macrophages are for administration to a subject intravenously by infusion. Suitably the transfected macrophages are for administration to a subject into the lung via intubation.

Suitably the transfected macrophages may be for administration to a subject in a single dose or in multiple doses depending on the achieved response and the subject tolerability to the treatment. Suitably doses may be given at intervals. Suitably the transfected macrophages may be for administration to a subject once per day, once every two days, once per week, once every 2 weeks, once per month, once every two months, once every 4 months, once every 6 months, once per year. The dosage schedule could vary depending on the subject's characteristics, and type of disease as is readily determined by a person skilled in the art.

Suitably the transfected macrophages are for administration to a subject in an effective amount. Suitably the transfected macrophages are for administration to a subject at a dose of about $10^5$ to $10^9$ cells, suitably about $10^6$ to $10^8$ cells, suitably about $10^7$ cells. Suitably the transfected macrophages are for administration in an amount selected from: between about 0.1 and about $1\times10^7$ cells per kilogram (cells/kg). The dose could vary depending on the subject's characteristics, and type of disease as is readily determined by a person skilled in the art.

The invention will now be described with reference to the following figures and examples.

FIGURES

Figure 1B:
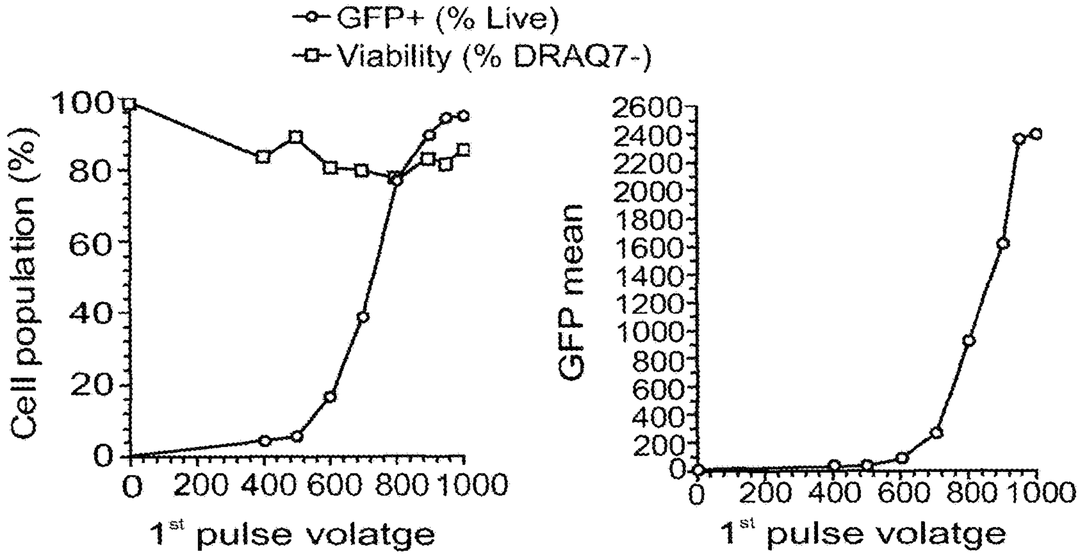
Figure 1C:
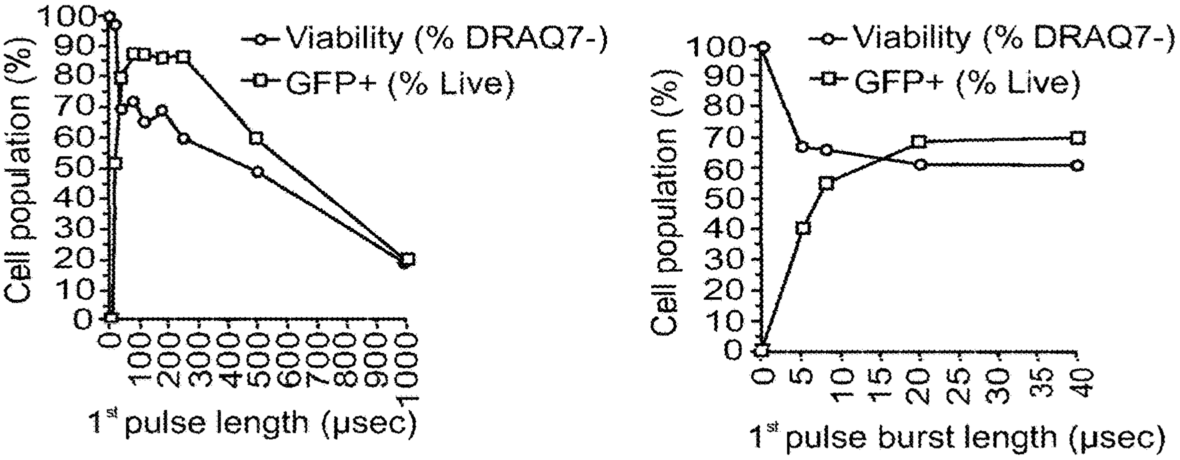

FIGS. 1A-1D show: Optimisation of electroporation first pulse parameters: Flow cytometry was used to assess viability (DRAQ-7 negative), efficiency (GFP+ cells) and intensity of expression of GFP (GFP mean) from the pMax-GFP vector 24 hours post-electroporation using unique first pulse parameters with a second low-voltage burst pulse (125 V, 8 μsec burst length for 23000 μsec), measured using Miltenyi MACSQuant flow cytometer. *$p<0.05$, $p<0.01$ one-way ANOVA with Tuckey's post-test (n=4 per group) FIG. 1A Comparison of viability, efficiency and expression intensity of pMax-GFP electroporation with different first pulse modes (square pulse, burst unipolar pulse or burst bipolar pulse). FIG. 1B Assessment of viability, efficiency and expression intensity of pMax-GFP with different first pulse voltages with a burst unipolar mode. FIG. 1C Assessment of viability and efficiency of pMax-GFP with different first pulse lengths with a burst unipolar mode, and different first pulse burst lengths with a burst unipolar mode measured with an Acea Novocyte flow cytometer. FIG. 1**D Assessment of viability and efficiency of pMax-GFP with single pulse in different modes measured with an Acea Novocyte flow cytometer.

Figure 2A:
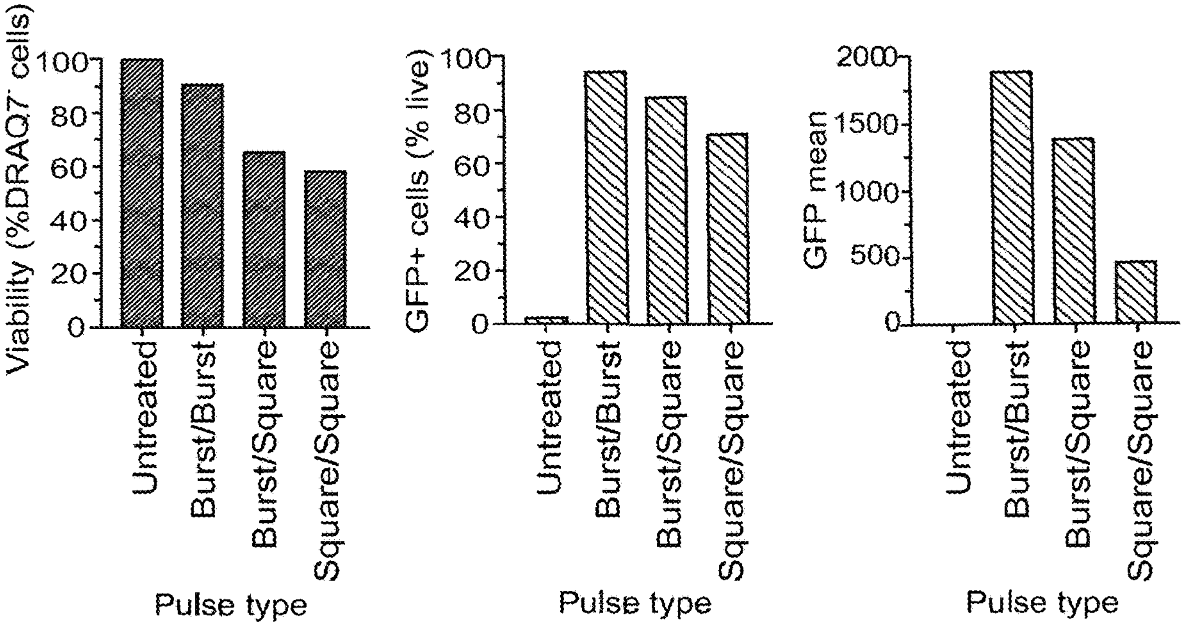
Figure 2B:
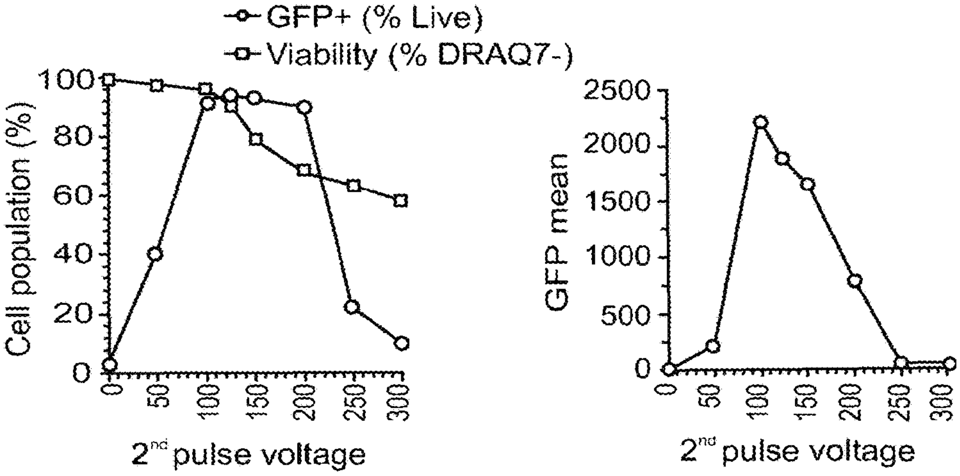
Figure 2C:
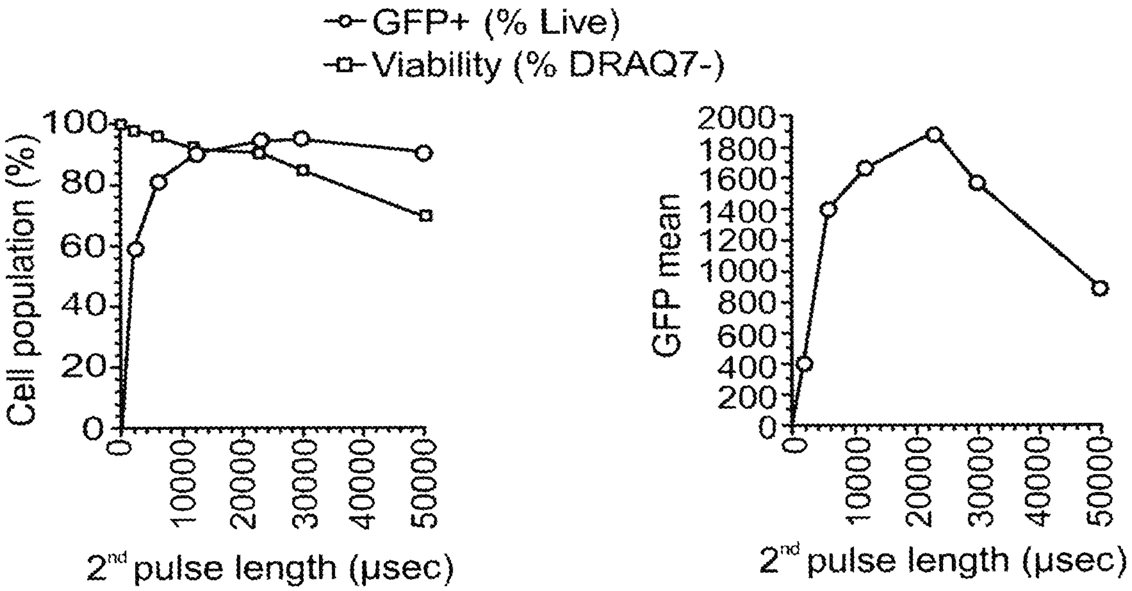
Figure 2D:
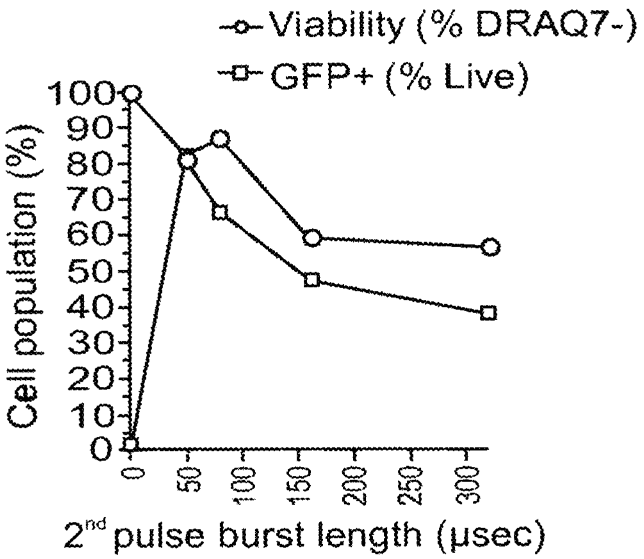

FIGS. 2A-2D show: Optimisation of second pulse parameters: Flow cytometry was used to assess viability (DRAQ-7 negative), efficiency (GFP+ cells) and intensity of expression of GFP (GFP mean) from the pMax-GFP vector 24 hours post-electroporation using unique second pulse parameters measured using Miltenyi MACSQuant flow cytometer. FIG. 2A Comparison of viability, efficiency and expression intensity of pMax-GFP electroporation with different combinations of first pulse (square pulse or burst unipolar pulse) and second pulse modes (square pulse or burst pulse). FIG. 2B Assessment of viability, efficiency and expression intensity of pMax-GFP with different second pulse voltages with a burst unipolar (first pulse) and burst (second pulse) configuration. FIG. 2C Assessment of viability, efficiency and expression intensity of pMax-GFP with different second pulse lengths with a burst unipolar (first pulse) and burst (second pulse) configuration. FIG. 2D Assessment of viability and efficiency of pMax-GFP with different second pulse burst lengths with a burst unipolar (first pulse) and burst (second pulse) configuration.

Figure 3A:
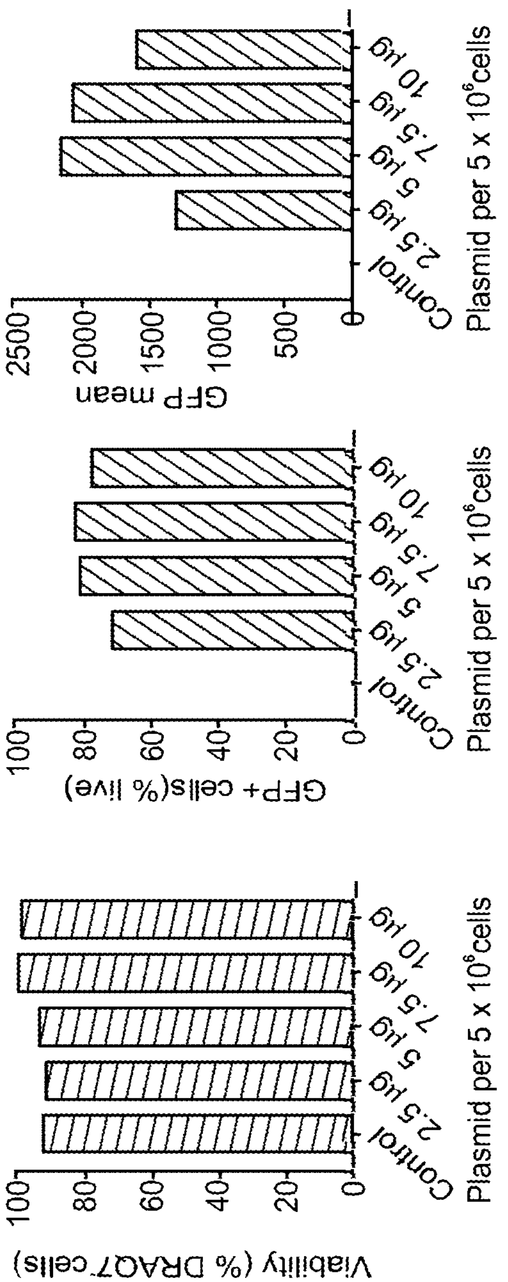
Figure 3B:
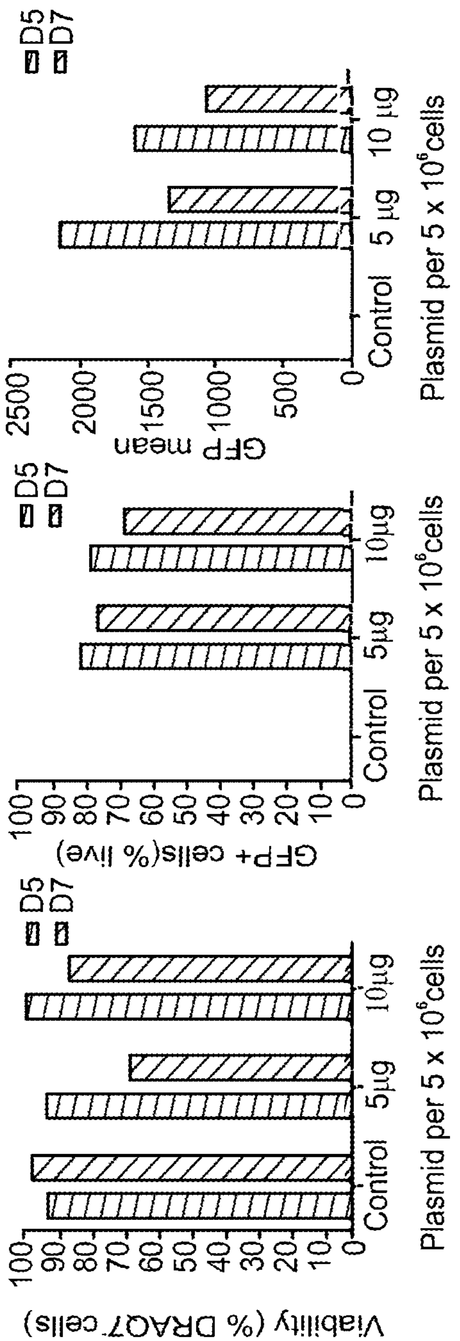

FIGS. 3A-3B show: Assessment of transfection efficiency with different amounts of plasmid: Flow cytometry was used to assess viability (DRAQ-7 negative), efficiency (GFP+ cells) and intensity of expression of GFP (GFP mean) from the pMax-GFP vector 24 hours post-electroporation measured using Miltenyi MACSQuant flow cytometer, testing FIG. 3A different amounts of pMax-GFP vector in 5-day differentiated macrophages. FIG. 3B Viability, efficiency and intensity was compared with different amounts of pMax-GFP vector in 5 versus 7-day differentiated macrophages.

Figure 4A:
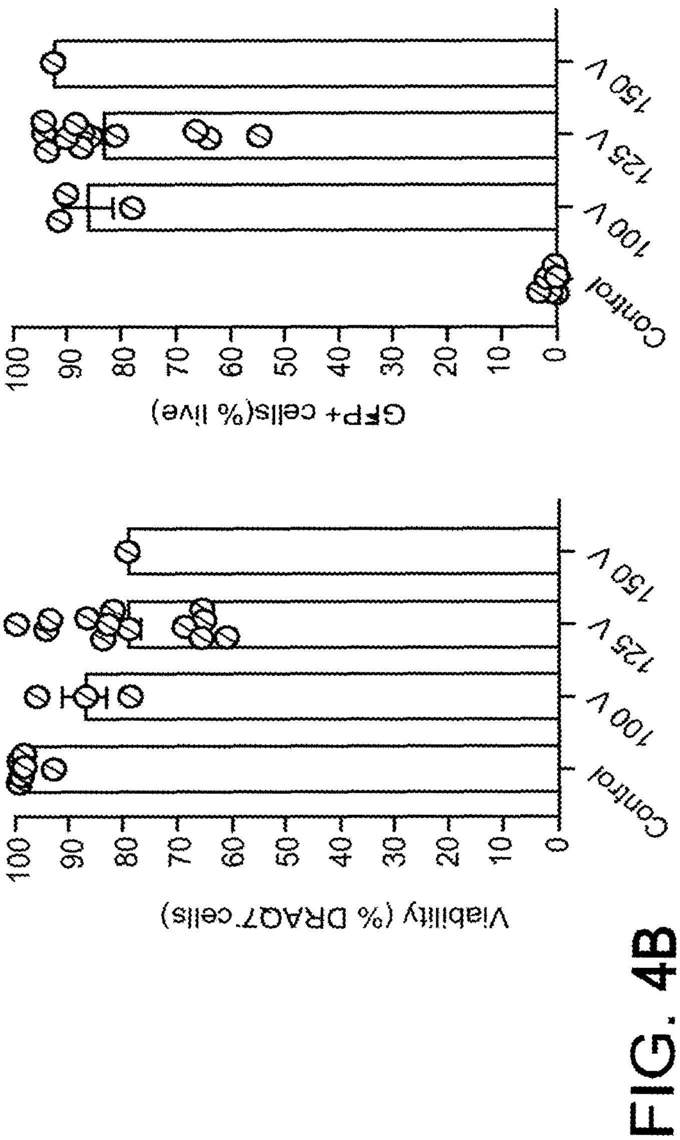
Figure 4B:
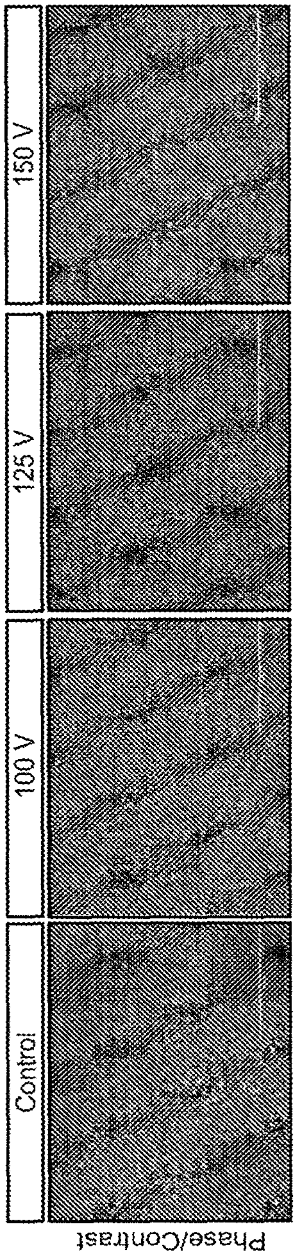

FIGS. 4A-4B show: Reproducibility of optimised transfection conditions: Flow cytometry was used to assess viability (DRAQ-7 negative) and efficiency (GFP+ cells) of expression of GFP from the pMax-GFP vector 24 hours post-electroporation using a 950V first pulse in burst unipolar mode, combined with a burst second pulse of 100V, 125V (ideal conditions) and 150V (non-ideal control). For ideal conditions, n=3 to 14 unique donor macrophages. FIG. 4B Phase/contrast microscopy shows healthy morphology of macrophages. Combined data from Miltenyi MACSQuant and Acea Novocyte flow cytometers. Scale bars represent 200 μm.

Figure 5A:
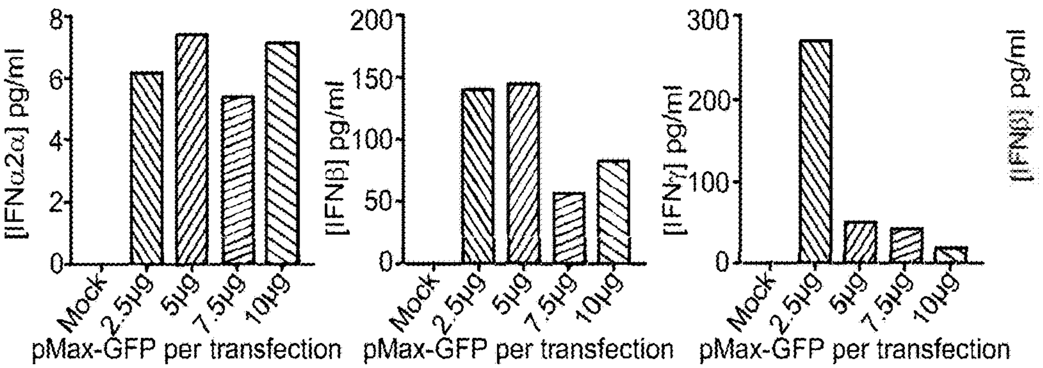
Figure 5B:
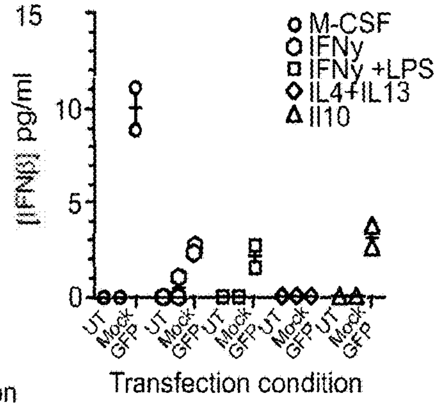
Figure 5C:
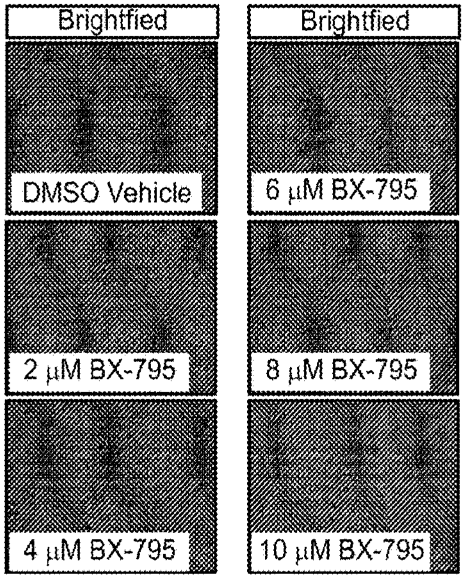
Figure 5D:
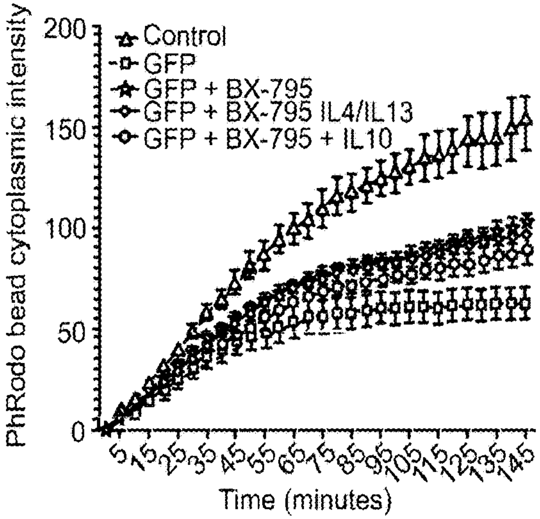
Figure 5E:
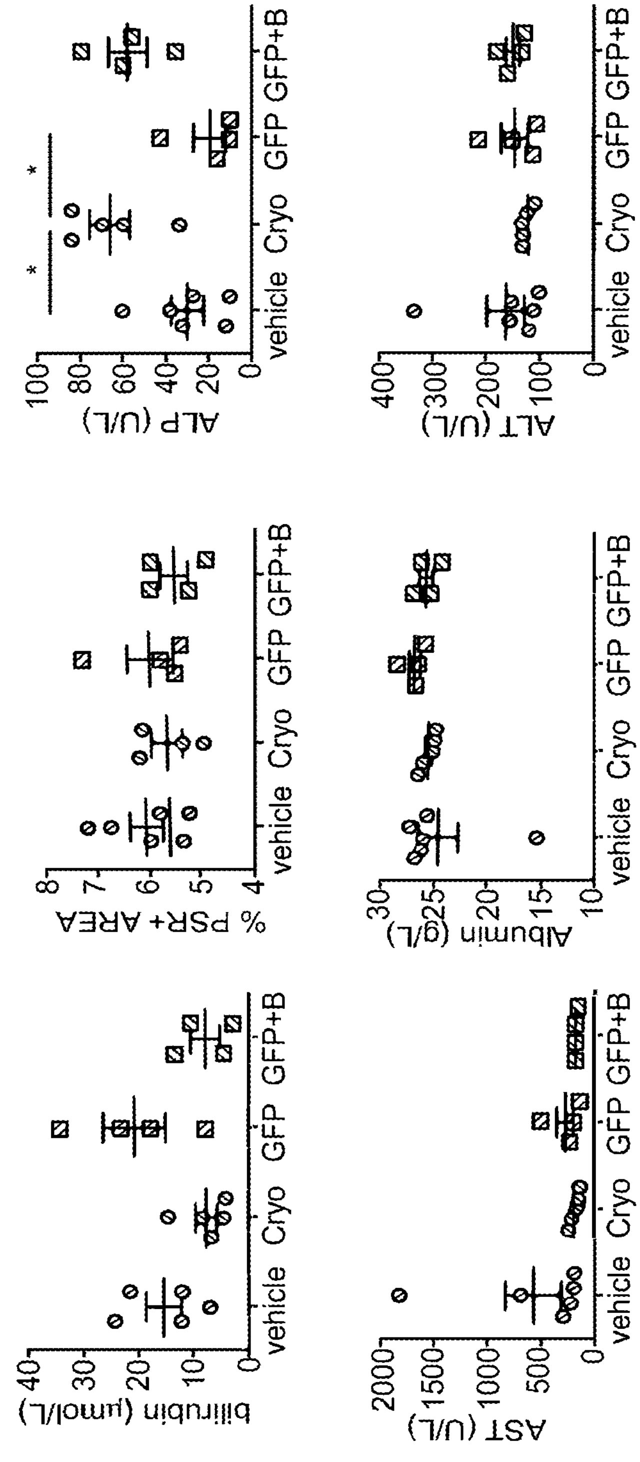

FIGS. 5A-5E show: Maintenance of macrophage function in vitro and in vivo with post-transfection and STING inhibitor treatment: FIG. 5A Analysis of secreted interferon (IFN) proteins in hMDMs electroporated with up to 10 μg pMax-GFP vector or electroporated without the presence of DNA (mock). FIG. 5B Analysis of secreted IFNβ protein in untransfected (UT), mock transfected (mock) or GFP transfected (GFP) hMDMs and cultured post-transfection with either M-CSF (control) or polarising factors IFNγ, IFNγ+LPS, IL4+IL13 or IL10 FIG. 5C Phase/contrast microscopy shows healthy morphology of macrophages using ideal conditions and treatment with STING inhibitor BX-795 versus DMSO control. FIG. 5D In vitro phagocytosis assay of untransfected hMDMs (control) versus GFP-transfected macrophages treated with BX-795 (GFP+BX-795), with M2-like polarising factors (GFP+BX-795+IL4/IL13 or IL10) or DMSO control (GFP). FIG. 5E Serum liver function tests and histological analysis of picrosirius red (PSR) staining of collagen in chronic $CCl_4$ mice treated with cryopreserved hMDM (cryo), GFP-transfected hMDM treated with DMSO (GFP), GFP-transfected hMDM treated with BX-795 (GFP+B) or PBS vehicle (vehicle). *$p<0.05$ one-way ANOVA.

Figure 6A:
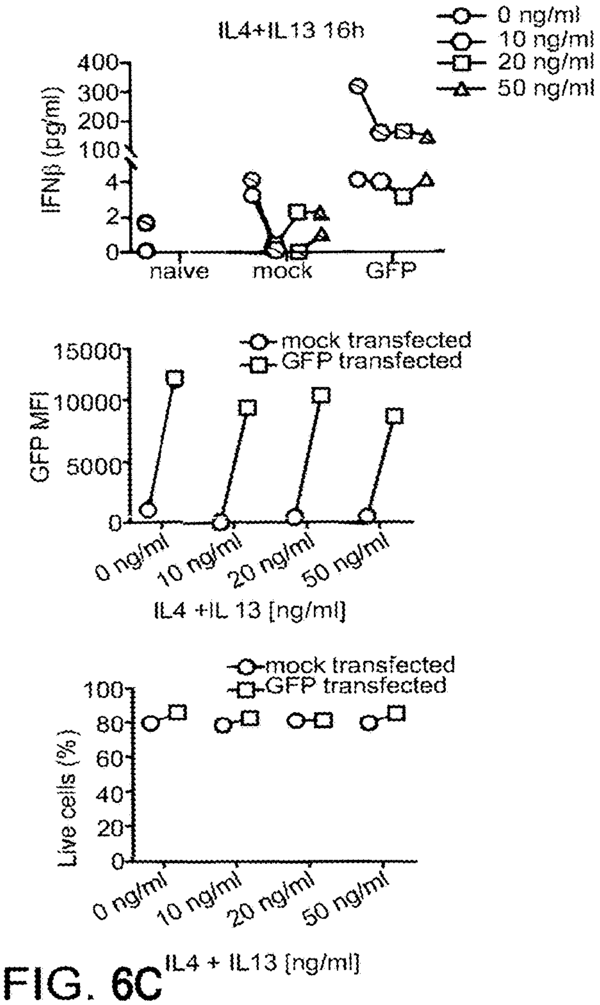
Figure 6B:
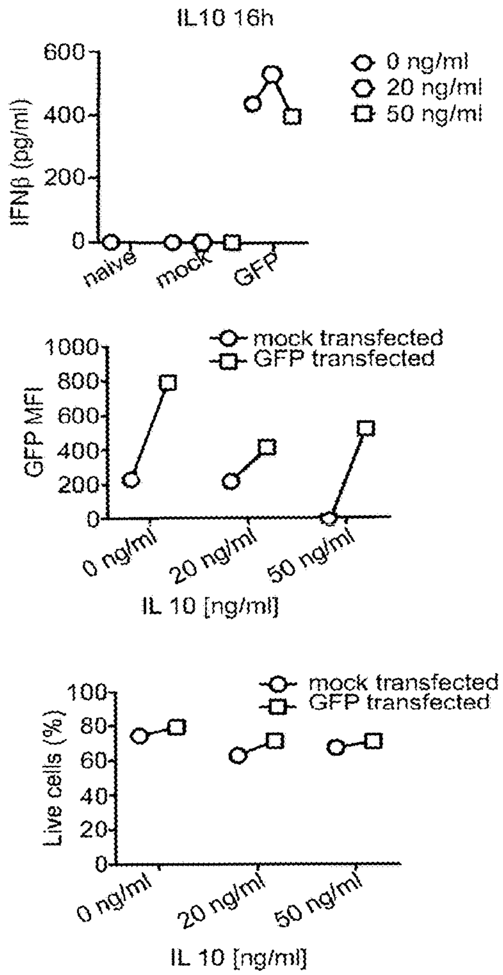
Figure 6C:
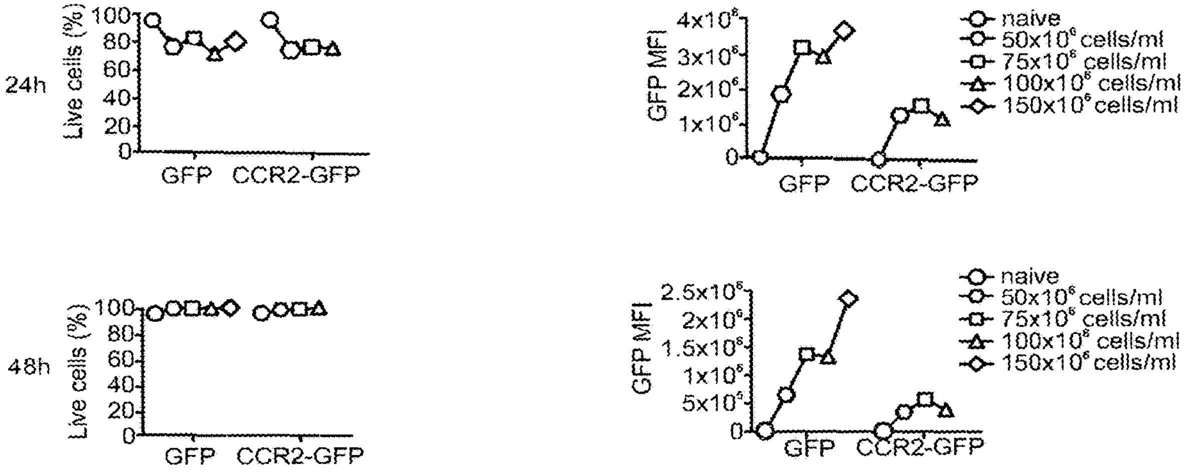

FIGS. 6A-6C show: Improvement of STING inhibition and transfection cell density: FIG. 6A ELISA for IFN-b was used to dose the protein in cell culture s/n from macrophages transfected with GFP and treated for 16 h with a combination of IL-4 and IL-13 at various concentration. Flow cytometry was used to determine the expression of GFP (GFP MFI) and the viability of macrophages transfected with GFP and treated for 16 h with a combination of IL-4 and IL-13 at various concentration. In all graph, every connected series of symbols (open or filled) represent a distinct donor. FIG. 6B ELISA for IFN-b was used to dose the protein in cell culture s/n from macrophages transfected with GFP and treated for 16 h with IL-10 at various concentration. Flow cytometry was used to determine the expression of GFP (GFP MFI) and the viability of macrophages transfected with GFP and treated for 16 h with IL-10 at various concentration. In all graph, every connected series of symbols represent a distinct donor. FIG. 6C Flow cytometry was used to quantify the expression of GFP (GFP MFI) and the viability of macrophages transfected with either GFP or a vector combining the expression of GFP or CCR2-GFP. In all graph, every symbol represents a distinct concentration of macrophages at the time of transfection, and the solid line connects data from the same donor. The same key applies for all graphs in FIG. 6C.

EXAMPLES

Materials and Methods

Generation and Characterization of Macrophages

Human monocyte-derived macrophages were generated from CD14+peripheral blood monocytes as previously described [16]. Briefly, peripheral blood mononuclear cells were isolated from whole blood buffy coat material from healthy volunteer donors according to established protocols [16]. CD14+ monocytes were enriched using CD14 CliniMACS beads (Miltenyi). Purity and differentiation were assessed as previously described [16]. Monocytes were cultured in TexMACS-GMP medium (Miltenyi) supplemented with GMP-grade M-CSF (100 ng/ml; RnD Systems) for 5 or 7 days and differentiation assessed by flow cytometry. Monocytes were CD45+, CD14+, CD15−, 25F9-low, CD206-low. Macrophages were CD45+, CD14+, 25F9+ and CD206+.

Electroporation

Monocyte-derived macrophages were harvested, counted and resuspended at a density of $5\times10^7$ cells/ml of CliniMACS Electroporation Buffer (Miltenyi). 25-100 μg/mL of pMax-GFP plasmid (Lonza) was mixed with the cell suspension for electroporation. For electroporation, 100 μl of cell/plasmid mix was introduced into 0.2 cm electroporation cuvettes and electroporation conducted with the CliniMACS Prodigy Electroporator (Miltenyi). Parameters assessed were 1st pulse voltage and type, and 2nd pulse voltage, type and length. Following electroporation, cells were cultured as above, with or without the STING inhibitor BX-795 (Invivogen) up to a concentration of 10 μM.

Test of an Alternative Method to Inhibit STING Pathway

Following electroporation, 200 μl sterile TexMACS was added to the cuvette and the cells were collected in a Falcon tube (pre-filled with 5 ml TexMACS) using a 18G needle attached to a 1 ml syringe. 500 μL TexMACS were added to the cuvette to collect any remaining cells.

The macrophage suspension was spun down at 300×g, 4° C. for 5 min. The supernatant was aspirated, and the cells were resuspended at concentration $4*10^6$ cells/mL in TexMACS supplemented with 100 ng/mL rh-M-CSF.

Macrophages were immediately treated with IL4 and IL13 (0, 10, 20 or 50 ng/mL). $10^5$ cells/well from each condition were seeded in a 96-well plate for flow cytometry/phagocytosis assessment. The remaining cells from each condition were seeded in 48-well plates for RNA analysis.

Optimisation of Cell Density at the Point of Electroporation

Day5 macrophages were spun down at 300*g, 4° C. for 5 min. The supernatant was discarded, and the cells were resuspended in electroporation buffer at the concentrations outlined below:

$50\times10^6$ cells/ml—$15\times10^6$ cells in 300 μl electroporation buffer (previously used cell density)

$75\times10^6$ cells/ml—$15\times10^6$ cells in 200 μl electroporation buffer $100\times10^6$ cells/ml—$15\times10^6$ cells in 150 μl electroporation buffer $150\times10^6$ cells/ml—$15\times10^6$ cells in 100 μl electroporation buffer 5 μg per $5\times10^6$ cells of GFP-expressing plasmid was added to the transfected cells immediately prior to electroporation. After electroporation as per protocol above, transfection efficiency was evaluated by flow cytometry, and RNA was preserved for future RNA analysis.

Assessment of Transfection Efficiency by Flow Cytometry 24 hours post-electroporation, cells were dissociated by pipetting up and down and a 200 μl aliquot placed in a flow cytometry tube for analysis. To assess viability, 1 μl of DRAQ-7 (Abcam) viability dye was added to the cell suspension and the cells were assessed by flow cytometry on a MACSQuant flow cytometer (Miltenyi), or Novocyte flow cytometer (Acea). Viability was assessed as the proportion of DRAQ7-negative cells. GFP-positivity was assessed compared to untransfected controls and expressed as the proportion of GFP+live (DRAQ-7-negative) cells. GFP intensity was assessed using mean fluorescence intensity.

Phagocytosis Assay

Cells were seeded in 96 well plates at a density of 200,000 per well in triplicate wells and left to adhere overnight. The following day, medium was aspirated and replaced with TexMACS medium containing NucBlue reagent (Invitrogen) and incubated for 30 min at 37° C. to stain nuclei. Medium was aspirated, cells washed in PBS, and then 100 μl PBS was added to cells. 100 μl of pHrodo *E. coli* red beads (diluted 1:10 in PBS) was added to the cells, and the cells were observed using an Operetta (PerkinElmer) to photograph fluorescence every 5 minutes over 145 minutes using a 40× objective. Images were analysed using Columbus. Nuclei were identified by NucBlue staining, and pHrodo red fluorescence intensity was measured in a cytoplasmic ring region around the nucleus. Fluorescence is reported as average pHrodo red fluorescence per nucleus.

Assessment of Secreted Proteins

Interferon proteins secreted into the medium of hMDMs were analysed using a U-PLEX Human Interferon Bundle kit on a MESO Quickplex SQ 120 according to the manufacturers' instructions (Meso Scale Discovery).

Mouse Experiments

NOD CB17 Prkdc/SCID mice were supplied by Charles River and housed in individually ventilated cages in a sterile animal facility with a 10-14-hours dark/light cycle and free access to food and water. All procedures were performed in accordance with UK Home Office guidelines (Animals [Scientific Procedures] Act 1986). Chronic liver fibrosis was induced in adult male mice over a 12-week period by twice weekly intraperitoneal injections of carbon tetrachloride ($CCl_4$) dissolved in sterile olive oil at a concentration of 0.2 mL/kg for the first week increasing to 0.4 mL/kg for further 10 weeks. One day after the 18th $CCl_4$ injection (9 weeks), mice were randomly allocated to receive either day5 cryopreserved (CP) hMDMs (n=5), day 5 macrophages transfected with pMax-GFP vector and cultured for a further 24 hours (GFP; n=4), day 5 macrophages transfected with pMax-GFP vector and cultured for a further 24 hours in medium supplemented with 5 μM BX-795 (GFP+B; n=4), or injected with saline (vehicle, n=6) injections via tail vein. The intra-splenic route would have ensured maximal cell delivery, but it does not model the administration route used in the phase I MATCH trial (day7 hMDMs in patients with chronic liver fibrosis) [17]. All hMDMs were suspended in sterile saline at a density of $5\times10^7$ cells/mL and 0.1 mL was injected via a 30-gauge needle (Myjector 0.3 mL syringes, Terumo). Injection of cells or saline was repeated at week 10 and week 11. 0.2 ml/kg $CCl_4$ administration continued for an additional week.

All mice were culled at the indicated time points using anaesthesia overdose followed by cervical dislocation as confirmatory method. Organs and blood were retrieved, processed and stored for further analysis: liver left lobe was snap frozen and stored at −80° C.; the other liver lobes were fixed in formalin 10% for 8 h and then included in paraffin blocks; kidneys, spleen, heart and lungs were fixed in formalin 10% for 8 h and then included in paraffin blocks; blood was collected in Eppendorf, left to sediment for 8 h and then spun at 10000×g for 10 minutes at room temperature to obtain serum, to be stored at −80° C.; blood collected in EDTA-coated tubes (Microvette CB300, Sarstedt) were used to collect 30? L of full blood to use for the analysis of the haematological parameters using the CellTac machine (Nihon Kohden).

Liver Function Tests on Sera

Serum chemistry was performed by measurement of alanine aminotransferase (ALT), aspartate aminotransferase (AST), alkaline phosphatase (ALP), total bilirubin, and serum albumin. ALT was measured using a commercial kit (Alpha Laboratories Ltd). AST and ALP were determined by a commercial kit (Randox Laboratories). Total bilirubin was determined by the acid diazo method described by Pearlman and Lee using a commercial kit (Alpha Laboratories Ltd). Mouse serum albumin measurements were determined using a commercial serum albumin kit (Alpha Laboratories Ltd). All kits were adapted for use on a Cobas Fara centrifugal analyzer (Roche Diagnostics Ltd). For all assays, intra-run precision was CV<4%. In some experiments, assays were run on plasma samples with the exception of ALP activity.

Histological Analysis

Picrosirius red (PSR) staining was performed according to standard protocols. Morphometric pixel analysis to quantify histological staining was performed. For fibrosis quantification PSR stained section were scanned to create a single image with Polaris slide scanner (Perkin Elmer). A second scan on the same machine was performed to obtain multi-spectral image acquisition on 10 to 15 fields/slide at 10× magnification. Multi-spectral images were analysed using the Trainable WEKA Segmentation mode using the InForm software (Perkin Elmer).

Results

1. Optimisation of First Pulse Parameters

We assessed the parameters of the first pulse in combination with a second lower voltage pulse, or with a single pulse in different modes. Initially we assessed the type of pulse using pre-set conditions for T-cell electroporation as baseline conditions (950V burst-bipolar first with burst second pulse). The types of first pulse assessed were the baseline 'burst-bipolar' mode, versus 'burst-unipolar' or 'square' pulse modes. We found that a first pulse in 'burst-unipolar' or 'square' mode provided similar transfection efficiencies (77.95±7.44% for 'burst-unipolar' vs 76.12±8.61% for 'square' pulse GFP+ cells) and viability (81.29±6.11% for 'burst-unipolar' vs 71.11±9.62% for 'square' pulse DRAQ7-cells) for macrophages, as measured by flow cytometry. Using a 'burst-bipolar' first pulse resulted in a lower transfection efficiency (61.11±13.85% GFP+ cells) and adequate viability (84.59±6.01% DRAQ7-cells; FIG. 1A). We next assessed the impact of first pulse voltage over the complete range (OV-1000V) of the Prodigy electroporator with a 'burst-unipolar' first pulse mode. Electroporation efficiency increased exponentially up to 900V, and plateaued between 900V and 1000V, without significant loss of cell viability (FIG. 1B). GFP expression was confirmed with fluorescence microscopy (not shown).

Figure 1D:
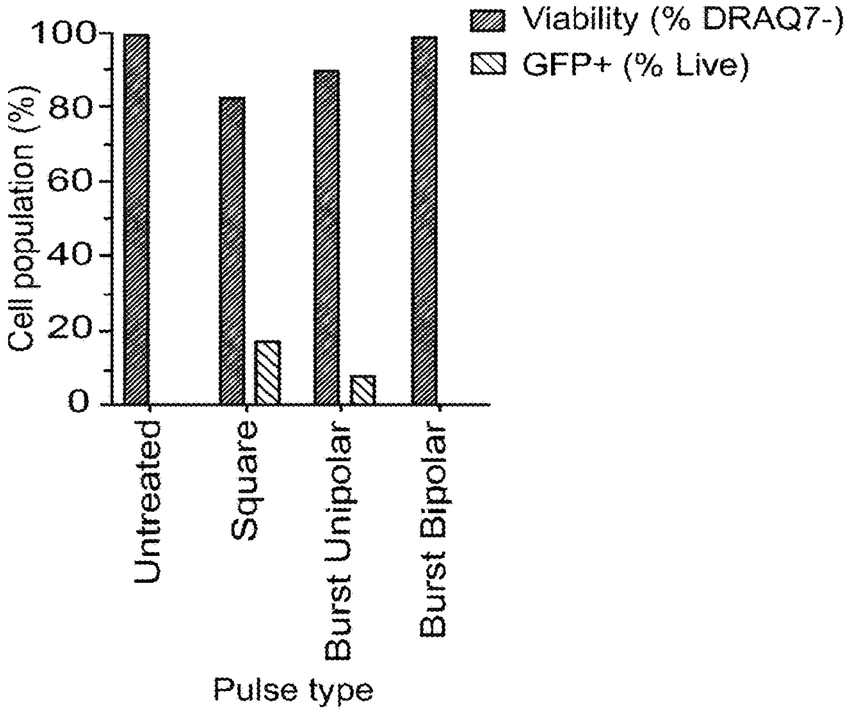

We next assessed the effects of first pulse length and burst length in burst-unipolar mode combined with a second low voltage burst pulse. Transfection efficiency increased up to 250 μsec, plateauing between 80-250 μsec, and viability decreased below 50% after 250 μsec (FIG. 1D). Transfection efficiency increased with increased burst length, while cell viability was decreased with transfection, plateauing from 5-40 μsec (FIG. 1C).

Having assessed a number of different first pulse types in combination with a second lower voltage pulse, we assessed efficiency and viability of macrophages subjected to a single electroporation pulse without a second lower voltage pulse. We observed low transfection efficiency (<20% GFP+ cells) with only a single pulse with square, burst-unipolar or burst-bipolar modes (FIG. 1D).

From these experiments, we determined that a dual pulse electroporation, with a first pulse of 900V-1000V in 'burst-unipolar' mode with a burst length of 5-40 μsec and a total pulse length of 80-250 μsec was ideal for introduction of the pMax-GFP vector into macrophages with minimal loss of viability.

2. Optimisation of Second Pulse Parameters

We assessed the effect of second pulse parameters on transfection efficiency and viability. Firstly, pulse combinations of ('1st pulse'+'2nd pulse') 'burst-unipolar'+'burst', 'burst-unipolar'+'square' and 'square'+'square' were assessed. A 'burst-unipolar' first pulse+'burst' second pulse gave the maximum viability (~90% live) and transfection efficiency (~94% GFP+). Although a 'burst-unipolar' first pulse+'square' second pulse resulted in a high transfection efficiency (~85% GFP+), a considerable reduction in viability (~65% live) was observed. The combination of 'square' first pulse+'square' second pulse resulted in the lowest transfection efficiency (~72% GFP+) and viability (~58% live; FIG. 2A). Using the optimised 950V 'burst-unipolar' first pulse we next assessed the effect of second pulse voltage between OV and 300V. Transfection efficiency increased exponentially up to 100V, plateauing from 100V-200V (~90%-94% GFP+ cells), then decreasing sharply up to 300V (~10% GFP+ cells). Viability remained high up to 125V (>90% live), then decreased to ~58% as voltage increased to 300V (FIG. 2B).

Finally, we assessed the effect of second pulse length over the range of 0 μsec-50000 μsec. Efficiency increased exponentially up to 6000 μsec, plateauing between 12000 μsec and 50000 μsec (~90%-95% GFP+ cells). However, viability decreased as the length of the pulse was increased, plateauing at ~90% from 12000 μsec to 23000 μsec, and reducing to ~69% at 50000 μsec (FIG. 2C). We also assessed the effect of second pulse burst length. We found that a second pulse burst length of 5-8 μsec gave the greatest efficiency (66.16-82.66% GFP+) and viability (82.22-86.66% DRAQ-7 negative; FIG. 2D). From these experiments, we determined that a second pulse of 100V-125V in 'burst' mode, with a burst length of 5-8 μsec a time of 12000-30000 μsec was ideal for introduction of the pMax-GFP vector into macrophages.

3. Assessment of the Effects of Macrophage Differentiation Protocols and Amount of DNA We assessed the impact on electroporation efficiency with different amounts of plasmid DNA in macrophages differentiated using a 5 day 'no feed' protocol, or the standard 7 days with one feed protocol. Viability was not affected by the amount of plasmid DNA used for electroporation. However, we observed a decrease in efficiency and intensity with less than 5 μg or more than 7.5 μg of plasmid DNA (FIG. 3A). Compared to day 5 macrophages, day 7 macrophages cells had reduced viability, GFP+ cells and GFP intensity when electroporated under the same conditions (FIG. 3B).

4. Reproducibility of Macrophage Electroporation

Having determined ideal conditions for electroporation of primary human macrophages, we combined data from all electroporation experiments to evaluate the reproducibility of our method (up to 14 individual donors) using a first burst unipolar pulse of 950V with a burst second pulse of 100V or 125V for 23000 μsec as 'ideal' conditions for electroporation. A second pulse voltage of 150V represented a 'non-ideal' condition for comparison. Although donor variation was observed, electroporation efficiency and viability was highly reproducible (FIG. 4A). Viability was high for ideal conditions (DRAQ-7-negative cells: 87.40±4.92%; n=3 for 100V, 79.40±3.28%; n=14 for 125V), with similar efficiency observed for both conditions (GFP-positive cells: 86.90±4.28%; n=3 for 100V, 84.15±3.37%; n=14 for 125V). Phase contrast microscopy showed healthy, intact morphology of macrophages 24 hours post-electroporation (FIG. 4B) and fluorescence microscopy demonstrated visible GFP expression in macrophages electroporated in the presence of pMax-GFP vector (FIG. 4B).

5. Maintenance of Post-Electroporation Macrophage Function by Inhibition of the Stimulator of Interferon Genes (STING) Pathway Upregulation of interferon (IFN) genes by the cGAS-cGAMP-STING pathway is a feature of macrophages encountering foreign DNA, and potentially affects function. Therefore, in order for macrophage genetic modification to be efficacious, a method to overcome this innate sensing mechanism must be employed. We tested the activation of this pathway by assessing the secretion of IFN proteins following electroporation of hMDMs with pMax-GFP. We observed secretion of IFNα2α, IFNβ and IFNγ with introduction of pMax-GFP vector into hMDMs (FIG. 5A). We also assessed secretion of STING pathway-induced IFNβ following electroporation in the presence or absence of the pMax-GFP vector ('GFP' or 'mock' respectively) compared to untransfected cells ('UT') and overnight culture with M1-like polarising stimuli (IFNγ or IFNγ+LPS) or M2-like polarising stimuli (IL4+IL13 or IL10). IFNβ secretion was induced by introduction of pMax-GFP into macrophage by electroporation, but not by electroporation alone. All polarising stimuli reduced the secretion of IFNβ, with IFNβ at undetectable control levels with the combination of IL4+IL13 in GFP-transfected cells (FIG. 5B). We utilised the STING inhibitor molecule BX-795 to inhibit this pathway and test in vitro function by measuring phagocytosis, and in vivo function by measuring the ability of cells to reduce liver fibrosis. Cells remained healthy and GFP-expressing up to 8 μM of BX-795, with some loss of cells at 10 μM (FIG. 5C). We measured phagocytic capacity of untransfected hMDMs or GFP-transfected hMDMs in the presence or absence of BX-795, and with BX-795 combined with polarization to M2-like alternatively activated cells with either IL4/IL13 or IL10. Phagocytic capacity, measured by the average fluorescence of pHRodo beads per cell, was approximately 41% of non-genetically modified hMDMs in GFP-transfected hMDMs treated with DMSO vehicle, and was recovered to approximately 66% of non-genetically modified hMDMs in GFP-transfected hMDMs treated with BX-795. Phagocytic capacity was not improved with the combination of M2-like polarising stimuli to BX-795 treatment (FIG. 5D). Mouse models of liver cirrhosis triggered by reiterative $CCl_4$-induced hepatocyte injury are a useful tool to test the safety and efficacy of cell therapy product. The induction phase of liver cirrhosis commonly last 4 to 12 weeks, depending on the extent of fibrosis desired [19-21]. We envisage our cell therapy being used in cases of advanced fibrosis therefore we chose to treat our mice for 12 weeks with $CCl_4$. Testing macrophage-based cell therapy products requires a xeno-transplant of human cell into mice. To avoid rejection, we opted to use immunodeficient mice. However, because these mice lack an appropriate immune response to liver fibrosis, they are unlikely to benefit from the paracrine effect of macrophage cell therapy on the mouse own immune response.

In the present pilot experiment, we compared the injection of $1\times10^6$ cryopreserved hMDMs, GFP-transfected hMDMs treated with DMSO vehicle or BX-795 at week 9, 10 and 11 of $CCl_4$ treatment. Control mice are injected with an equivalent volume of saline only (vehicle). Mice are culled at week 12 and blood and organs collected for further analysis. Histological analysis of the quantity of fibrosis in the liver by PSR staining and quantification revealed an average decrease in fibrosis of 6.3% in cryopreserved hMDMs treated, and 8.5% in GFP-transfected hMDMs treated with BX-795 proportionally to saline treated mice. However, no difference was observed between GFP-transfected hMDMs treated with DMSO vehicle (FIG. 5E). Sera analysis confirmed a positive effect of the cryopreserved and GFP-transfected hMDMs treated with BX-795: Results show a trend towards a decrease in liver enzymes ALT and AST and, more importantly, a reduction in bilirubin circulating levels (FIG. 5E), one of the main factors in monitoring the results of macrophage cell therapy in the clinic [4]. No change in circulating GLDH and Albumin was noted.

These data show that the combination of introducing DNA into macrophages via electroporation with treatment with an inhibitor of the innate DNA sensing mechanism enables the production of genetically modified macrophages that are functional in vitro and in vivo and are safe for use in animal models of liver disease.

6. Maintenance of Post-Electroporation Macrophage Function by Inhibition of the Stimulator of Interferon Genes (STING) Pathway Starting from the results expressed in FIG. 5B, we postulated that treatment of macrophages post-transfection with combination of IL4 and IL13 or IL10 could be used as an alternative strategy to inhibit the STING pathway, thereby improving macrophage phenotype and function.

To this end, we treated macrophages with 10 ng/ml, 20 ng/ml or 50 ng/ml of a combination of IL4 and IL13, and with 20 ng/ml or 50 ng/ml of IL10. We transfected macrophages with GFP, and we measured IFNβ production in cell culture supernatants after 16 h from transfection (GFP), from electroporation only (mock) or from plating without transfection or electroporation (control). Treatment with IL4+IL13 resulted in a trend towards reduction of IFN-β production in both donors (control mean=55.39 μg/ml; 10 ng/ml mean=40.39 μg/mL; 20 ng/ml mean=42.24 μg/mL; 50 ng/ml mean=39.64 μg/mL) (FIG. 6A). Various concentration of IL4+IL13 induced only minor changes in GFP expression, with 20 ng/ml being the most conservative condition (GFP MFI; FIG. 6A; Control (0 ng/ml) GFP transfected=12636; 10 ng/ml GFP transfected=9909; 20 ng/ml GFP transfected=11045; 50 ng/ml=9226). Viability was also unaffected by IL4+IL13 treatment (Live %; FIG. 6A; Control (0 ng/ml) GFP transfected=87.07%; 10 ng/mL GFP transfected=83.34%; 20 ng/ml GFP transfected=82%; 50 ng/mL=85.88%).

We also treated macrophages with 20 ng/ml or 50 ng/ml of a combination of IL10, and with 20 ng/ml or 50 ng/ml of IL10. We transfected macrophages with GFP, and we measured IFNβ production in cell culture supernatants after 16 h from transfection (GFP), from electroporation only (mock) or from plating without transfection or electroporation (control). Treatment with IL10 resulted in a trend towards reduction of IFN-β production only at a concentration of 50 ng/ml (control mean=431.47 μg/ml; 20 ng/ml mean=524.16 μg/mL; 50 ng/ml mean=392.39 μg/mL) (FIG. 6B). Various concentration of IL10 had a slight effect in reducing GFP expression (GFP MFI; FIG. 6B; Control (0 ng/ml) GFP transfected=786; 20 ng/ml GFP transfected=418; 50 ng/ml=531). Viability was largely unaffected by IL10 treatment (Live %; FIG. 6B; Control (0 ng/ml) GFP transfected=78.69%; 20 ng/ml GFP transfected=70.69%; 50 ng/ml=70.36%).

We also optimised the electroporation concentration of macrophages. We compared 50×10$^6$/mL (concentration used so far) with 75×10$^6$/ml; 100×10$^6$/mL; and 150×10$^6$/mL. We transfected a plasmid expressing GFP (~3.5 kb) and we record results at 24 h and 48 h post-transfection. We also transfected a plasmid encoding for CCR2 and GFP (i.e. a larger plasmid, ~6 kb). We tested CCR2-GFP at 24 h and 48 h using 50×10$^6$/mL (concentration used so far); 75×10$^6$/mL; and 100×10$^6$/mL, but not at 150×10$^6$/mL, due to limitations in the available cell numbers. 75×10$^6$/mL and 150×10$^6$/mL offered a significant increase in GFP expression at 24 h and 48 h, using the GFP plasmid, as assessed by flow cytometry (FIG. 6C; see below for a table with the raw MFI values at 24 h). Viability was also unaffected by the concentration at the point of electroporation (FIG. 6C; see below for a table with the raw percentage values at 24 h). 75×10$^6$/mL offered a significant increase in GFP expression at 24 h and 48 h, using the GFP-CCR2 plasmid (150×10$^6$/mL not assessed—n.a.—using this plasmid), as measured by flow cytometry (FIG. 6C; see below for a table with the raw MFI values at 24 h). Viability was also unaffected by the concentration at the point of electroporation (FIG. 6C; see below for a table with the raw percentage values at 24 h).

| | 50 × 10$^6$/mL | | 75 × 10$^6$/mL | | 100 × 10$^6$/mL | | 150 × 10$^6$/mL | |
|---|---|---|---|---|---|---|---|---|
| | GFP | CCR2-GFP | GFP | CCR2-GFP | GFP | CCR2-GFP | GFP | CCR2-GFP |
| GFP MFI | 1859591 | 1252692 | 3190158 | 1511828 | 2942530 | 1145144 | 3665920 | n.a. |
| Viability (%) | 76.06 | 73.03 | 81.75 | 75.55 | 71.38 | 74.89 | 79.77 | n.a. |

Raw Percentage Values at 24 h Post-Transfection

Collectively, these data show that various STING inhibition strategy can be deployed without affecting transgene expression and macrophage viability. Finally, these data support the possibility of using a broad range of cell concentration at the point of electroporation, a feature useful when devising treatment courses with different cell dosages.

CONCLUSIONS

The development of the method of the invention enables the efficient and reproducible production of genetically modified GMP-grade human primary monocyte-derived macrophages. We have described the effects of different first and second pulse parameters on cell viability and efficiency of introduction of genetic material into macrophages. Unlike previous methods of introducing genetic material into macrophages, we demonstrate the ideal conditions which produce efficient transgene expression, without compromising cell viability, and our experiments provide a robust framework for the optimisation of introduction and expression of vectors encoding different genes of interest. Critically, the method of the invention does not use virus to introduce genetic material, is efficacious on mature cells, are functional with in vitro assay and in vivo transfer in a liver disease model and complies with practices compatible with manufacture and delivery of these cells to patients.

EQUIVALENTS

Those skilled in the art will recognise or be able to ascertain using no more than routine experimentation, equivalents of the specific embodiments described herein. Such equivalents are intended to be encompassed by the following claims. Any combination of the embodiments disclosed in the any plurality of the dependent claims or Examples is contemplated to be within the scope of the disclosure.

INCORPORATION BY REFERENCE

The disclosure of each and every patent, patent application publication, and scientific publication referred to herein is specifically incorporated herein by reference in its entirety, as are the contents of its Figures.

REFERENCES

[1] Kochenderfer J N, Wilson W H, Janik J E, Dudley M E, Stetler-Stevenson M, Feldman S A, et al. Eradication of B-lineage cells and regression of lymphoma in a patient treated with autologous T cells genetically engineered to recognize CD19. Blood 2010; 116:4099-4102.
[2] Thomas J A, Pope C, Wojtacha D, Robson A J, Gordon-Walker T T, Hartland S, et al. Macrophage therapy for murine liver fibrosis recruits host effector cells improving fibrosis, regeneration, and function. Hepatology 2011; 53:2003-2015.
[3] Moore J K, Mackinnon A C, Wojtacha D, Pope C, Fraser A R, Burgoyne P, et al. Phenotypic and functional characterization of macrophages with therapeutic potential generated from human cirrhotic monocytes in a cohort study. Cytotherapy 2015; 17:1604-1616.
[4] Moroni F, Dwyer B J, Graham C, Pass C, Bailey L, Ritchie L, et al. Safety profile of autologous macrophage therapy for liver cirrhosis. Nat Med 2019; 25:1560-1565.
[5] Moyes K W, Lieberman N A, Kreuser S A, Chinn H, Winter C, Deutsch G, et al. Genetically Engineered Macrophages: A Potential Platform for Cancer Immunotherapy. Hum Gene Ther 2017; 28:200-215.

[6] Bear A S, Morgan R A, Cornetta K, June C H, Binder-Scholl G, Dudley M E, et al. Replication-competent retroviruses in gene-modified T cells used in clinical trials: is it time to revise the testing requirements? Mol Ther 2012; 20:246-249.

[7] Milone M C, O'Doherty U. Clinical use of lentiviral vectors. Leukemia 2018; 32:1529-1541.

[8] Lopez-Yrigoyen M, Yang C T, Fidanza A, Cassetta L, Taylor A H, McCahill A, et al. Genetic programming of macrophages generates an in vitro model for the human erythroid island niche. Nat Commun 2019; 10:881.

[9] Ackermann M, Kuhn A, Kunkiel J, Merkert S, Martin U, Moritz T, et al. Ex vivo Generation of Genetically Modified Macrophages from Human Induced Pluripotent Stem Cells. Transfus Med Hemother 2017; 44:135-142.

[10] Andrews P W, Ben-David U, Benvenisty N, Coffey P, Eggan K, Knowles B B, et al. Assessing the Safety of Human Pluripotent Stem Cells and Their Derivatives for Clinical Applications. Stem Cell Reports 2017; 9:1-4.

[11] Jensen K, Anderson J A, Glass E J. Comparison of small interfering RNA (siRNA) delivery into bovine monocyte-derived macrophages by transfection and electroporation. Vet Immunol Immunopathol 2014; 158:224-232.

[12] Ng Y S, Roca H, Fuller D, Sud S, Pienta K J. Chemical transfection of dye-conjugated microRNA precursors for microRNA functional analysis of M2 macrophages. J Cell Biochem 2012; 113:1714-1723.

[13] Warwick C A, Usachev Y M. Culture, Transfection, and Immunocytochemical Analysis of Primary Macrophages. Methods Mol Biol 2017; 1554:161-173.

[14] Maeß M B, Keller A A, Rennert K, Mosig A, Lorkowski S. Optimization of the transfection of human THP-1 macrophages by application of Nunc UpCell technology. Anal Biochem 2015; 479:40-42.

[15] Siegert I, Schatz V, Prechtel A T, Steinkasserer A, Bogdan C, Jantsch J. Electroporation of siRNA into mouse bone marrow-derived macrophages and dendritic cells. Methods Mol Biol 2014; 1121:111-119.

[16] Fraser A R, Pass C, Burgoyne P, Atkinson A, Bailey L, Laurie A, et al. Development, functional characterization and validation of methodology for GMP-compliant manufacture of phagocytic macrophages: A novel cellular therapeutic for liver cirrhosis. Cytotherapy 2017; 19:1113-1124.

[17] Moroni F, Dwyer B J, Graham C, Pass C, Bailey L, Ritchie L, et al. Safety profile of autologous macrophage therapy for liver cirrhosis. Nat Med 2019.

[18] Pearlman F C, Lee R T. Detection and measurement of total bilirubin in serum, with use of surfactants as solubilizing agents. Clin Chem 1974; 20:447-453.

[19] Montfort I, Perez-Tamayo R. Collagenase in experimental carbon tetrachloride cirrhosis of the liver. Am J Pathol 1978; 92:411-420.

[20] Perez Tamayo R. Is cirrhosis of the liver experimentally produced by CCl4 and adequate model of human cirrhosis? Hepatology 1983; 3:112-120.

[21] Shi J, Aisaki K, Ikawa Y, Wake K. Evidence of hepatocyte apoptosis in rat liver after the administration of carbon tetrachloride. Am J Pathol 1998; 153:515-525.

The invention claimed is:

1. An in vitro method of transfecting a human macrophage with genetic material, the method comprising the steps of:

(a) contacting a human macrophage with genetic material;

(b) electroporating the macrophage with a first pulse phase, wherein the first pulse phase comprises a burst of unipolar pulses, wherein each pulse is between 750-1000V, and wherein the first pulse phase lasts for a total period of between 20-500 μs; and (c) electroporating the macrophage with a second pulse phase, wherein the second pulse phase comprises a burst of unipolar pulses, wherein each pulse is between 50-225V, and wherein the second pulse phase lasts for a total period of 2000-50000 μs.

2. The method according to claim 1, wherein each pulse in the first pulse phase is selected from:

i) between 800-1000V;
ii) between 850-1000V;
iii) between 900-1000V;
iv) between 950-1000V; or
v) about 950V; and/or wherein the first pulse phase is for a total period of time selected from:

i) between 40-180 μs;
ii) between 80-120 μs; or
iii) about 120 μs.

3. The method according to claim 1, wherein each pulse in the second pulse phase is selected from:

i) between 80-200V;
ii) between 85-175V;
iii) between 90-150V;
iv) between 95-125V; or
v) about 100-125V; and/or wherein the second pulse phase is for a total period of time selected from:

i) between 11000-30000 μs;
ii) between 12000-30000 μs;
iii) between 11000-25000 μs;
iv) between 12000-25000 μs;
v) between 11000-23000 μs;
vi) between 12000-23000 μs; or
vii) about 23000 μs.

4. The method according to claim 1, wherein the genetic material comprises one or more nucleic acids encoding:

one or more genes of interest and/or regulatory elements; or a homologous or heterologous gene of interest.

5. The method according to claim 1, wherein the genetic material is comprised on a vector.

6. The method according to claim 1, wherein the human macrophages are human monocyte-derived macrophages.

7. The method according to claim 1, wherein the human macrophage is present in a solution at a cell density selected from:

i) between $1\times10^5$ to $1\times10^9$ cells/mL;
ii) between $5\times10^5$ to $8\times10^8$ cells/mL;
iii) between $1\times10^6$ to $6\times10^8$ cells/mL;
iv) between $5\times10^6$ to $5\times10^8$ cells/mL;
v) between $5\times10^7$ to $1.5\times10^8$ cells/mL;
vi) between $1\times10^7$ to $1\times10^9$ cells/mL; or
vii) $5\times10^7$ cells/mL; and/or wherein the genetic material is present in a solution at a concentration selected from:

i) between 1 to 10 μg per $5\times10^6$ macrophage cells;
ii) between 3 to 9 μg per $5\times10^6$ macrophage cells;
iii) between 4 to 8 μg per $5\times10^6$ macrophage cells; or
iv) between 5 to 7.5 μg per $5\times10^6$ macrophage cells.

* * * * *